United States Patent
Galimberti et al.

(10) Patent No.: US 11,098,012 B2
(45) Date of Patent: Aug. 24, 2021

(54) ADDUCTS OF PYRROLE DERIVATIVES TO CARBON ALLOTROPES

(71) Applicants: PIRELLI TYRE S.p.A, Milan (IT); POLITECNICO DI MILANO, Milan (IT)

(72) Inventors: Maurizio Stefano Galimberti, Milan (IT); Vincenzina Barbera, Milan (IT)

(73) Assignee: PIRELLI TYRE S.p.A., Milan (IT)

( * ) Notice: Subject to any disclaimer, the term of this patent is extended or adjusted under 35 U.S.C. 154(b) by 0 days.

(21) Appl. No.: 16/347,069

(22) PCT Filed: Nov. 9, 2017

(86) PCT No.: PCT/IB2017/057001
§ 371 (c)(1),
(2) Date: May 2, 2019

(87) PCT Pub. No.: WO2018/087685
PCT Pub. Date: May 17, 2018

(65) Prior Publication Data
US 2020/0055820 A1     Feb. 20, 2020

(30) Foreign Application Priority Data
Nov. 9, 2016 (IT) ..................... IT102016000113012

(51) Int. Cl.
| C07D 207/323 | (2006.01) |
| C07D 403/06 | (2006.01) |
| C07F 7/18 | (2006.01) |
| C07D 207/325 | (2006.01) |
| C01B 32/21 | (2017.01) |
| C01B 32/198 | (2017.01) |

(52) U.S. Cl.
CPC ........ *C07D 207/323* (2013.01); *C01B 32/198* (2017.08); *C01B 32/21* (2017.08); *C07D 207/325* (2013.01); *C07D 403/06* (2013.01); *C07F 7/1804* (2013.01); *C01B 2204/04* (2013.01)

(58) Field of Classification Search
CPC ............ C07D 207/323; C07D 207/325; C07D 403/06; C01B 32/21; C01B 32/198; C01B 2204/04; C07F 7/1804
USPC ....................................................... 548/524
See application file for complete search history.

(56) References Cited

U.S. PATENT DOCUMENTS

| 2006/0045838 A1 | 3/2006 | Malenfant et al. |
| 2017/0275169 A1 | 9/2017 | Galimberti et al. |

FOREIGN PATENT DOCUMENTS

WO    WO 2016/050887 A1    4/2016

OTHER PUBLICATIONS

International Search Report form the European Patent Office in corresponding International Application No. PCT/IB2017/057001 dated Jan. 11, 2018.
Written Opinion of the International Searching Authority from the European Patent Office in corresponding International Application No. PCT/IB2017/057001 dated Jan. 11, 2018.
Nandeesh, K.N. et al., "Recyclable, Graphite-Catalyzed, Four-Component Synthesis of Functionalized Pyrroles", Synthetic Communications, vol. 44, No. 8, 2014, pp. 1103-1110.

*Primary Examiner* — Kristin A Vajda
(74) *Attorney, Agent, or Firm* — Finnegan, Henderson, Farabow, Garrett & Dunner, L.L.P.

(57) ABSTRACT

Adducts are described formed between pyrrole derivatives of formula (I) an carbon allotropes in which the carbon is $sp^2$ hybridized, such as for example carbon nanotubes, graphene or nanographites, carbon black. The pyrrole derivatives bear substituents on the nitrogen atom suitable for improving the physicochemical characteristics of said allotropes. A process for preparing said adducts is also described. The adducts are formed with a pyrrole of formula (I) wherein X is selected from the group consisting of: The other substituents are as defined in the claims.

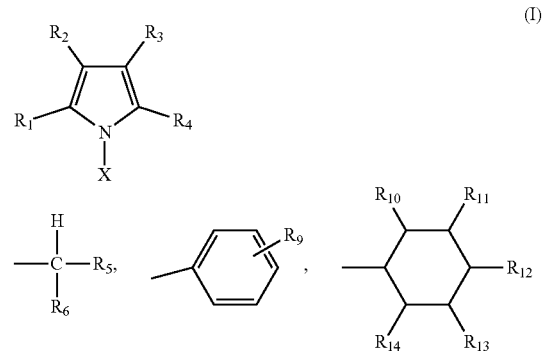

9 Claims, 9 Drawing Sheets

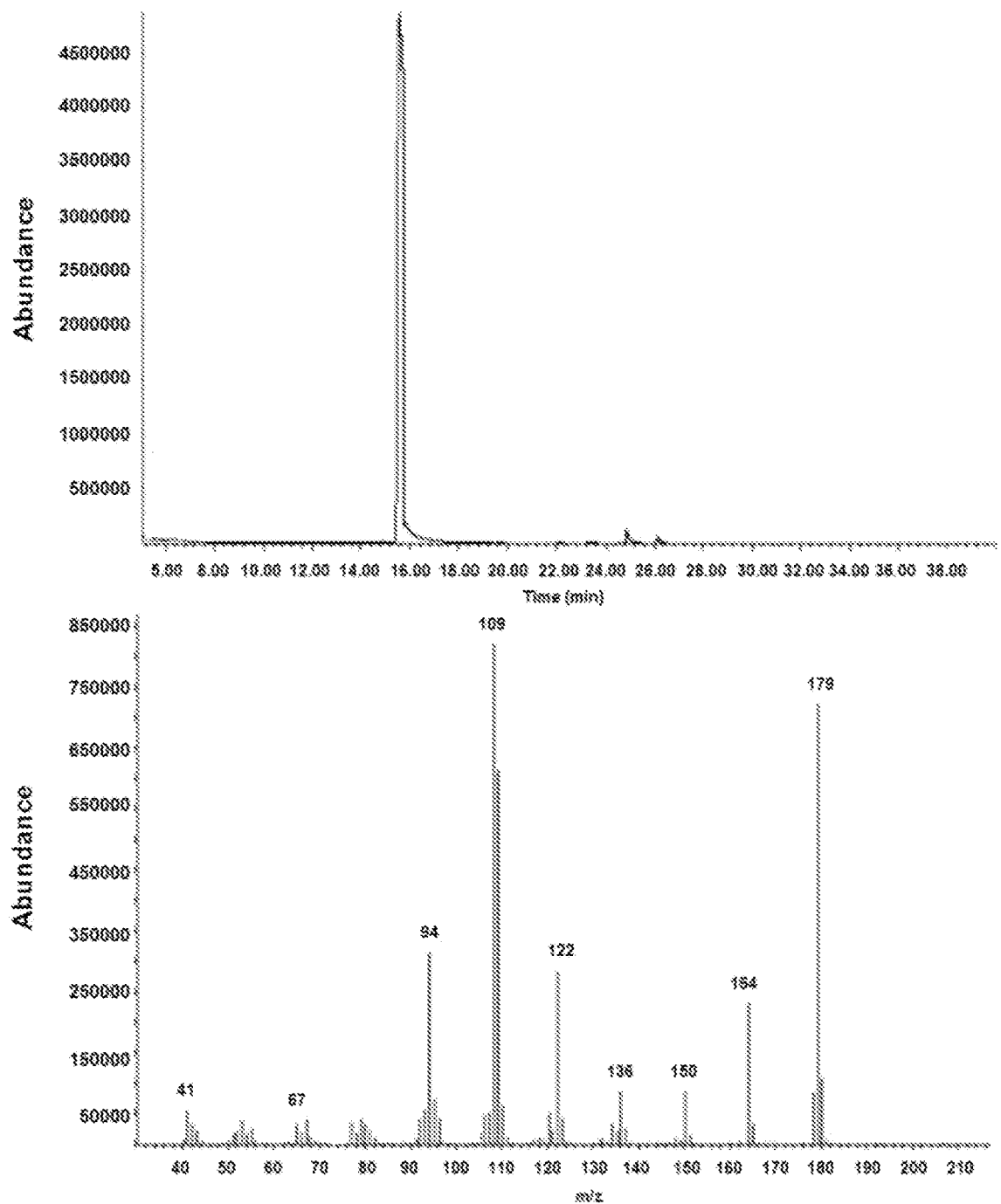
Fig. 1. GC-MS of 1-hexyl-2,5-dimethyl-1*H*-pyrrole

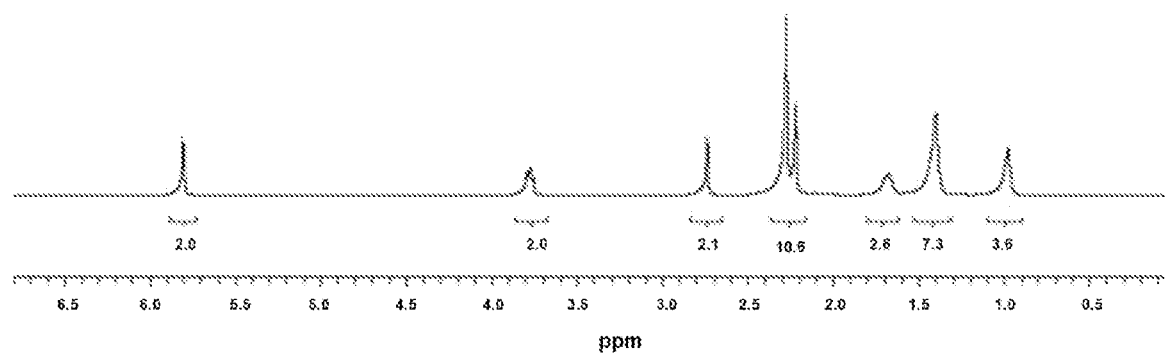
Fig. 2. $^1$H NMR spectrum, 400 MHz in CDCl$_3$, of 1-hexyl-2,5-dimethyl-1$H$-pyrrole

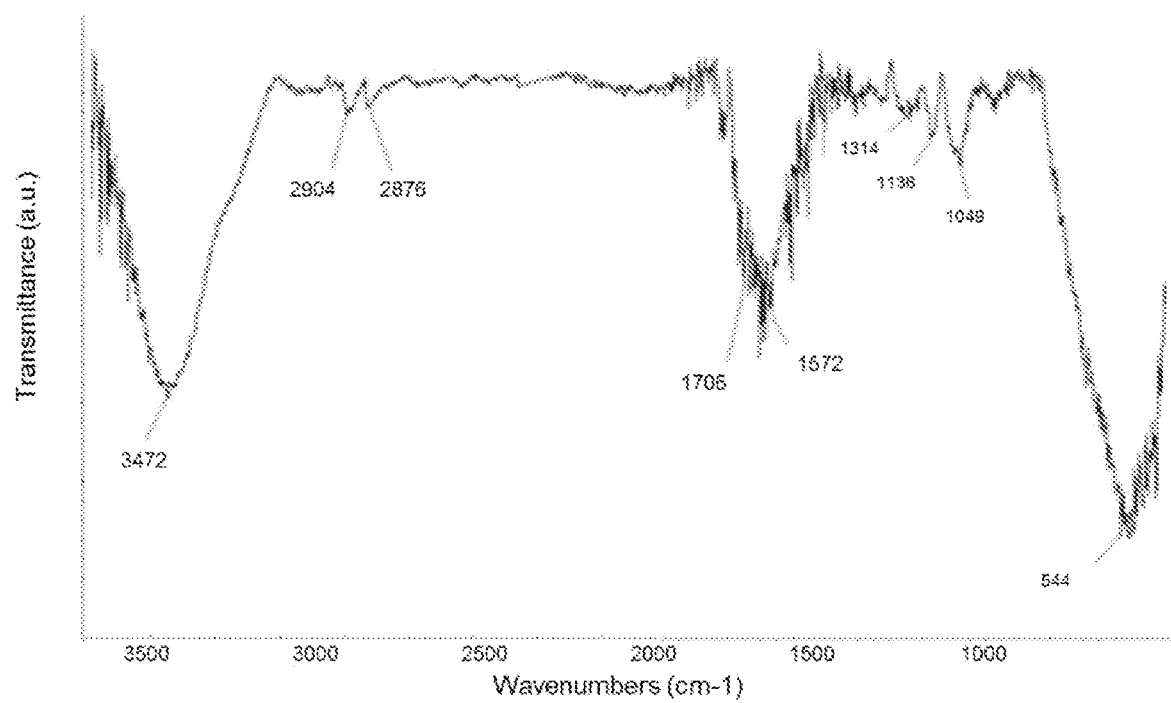
Fig. 3. FT-IR spectrum of the adduct of 1-hexyl-2,5-dimethyl-1$H$-pyrrole with CB N 326

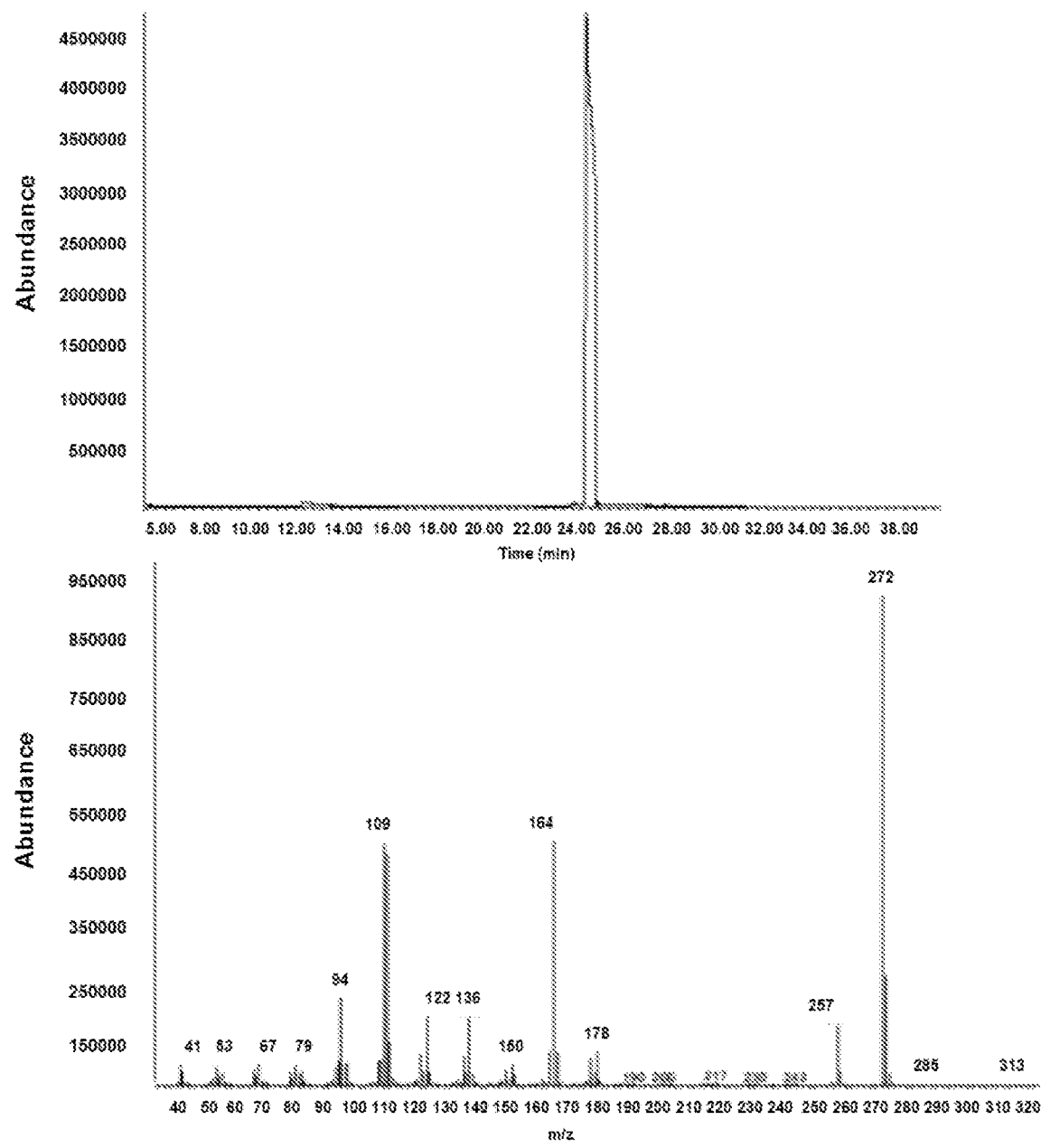
Fig. 4. GC-MS of 1,6-bis(2,5-dimethyl-1*H*-pyrrol-1-yl)hexane

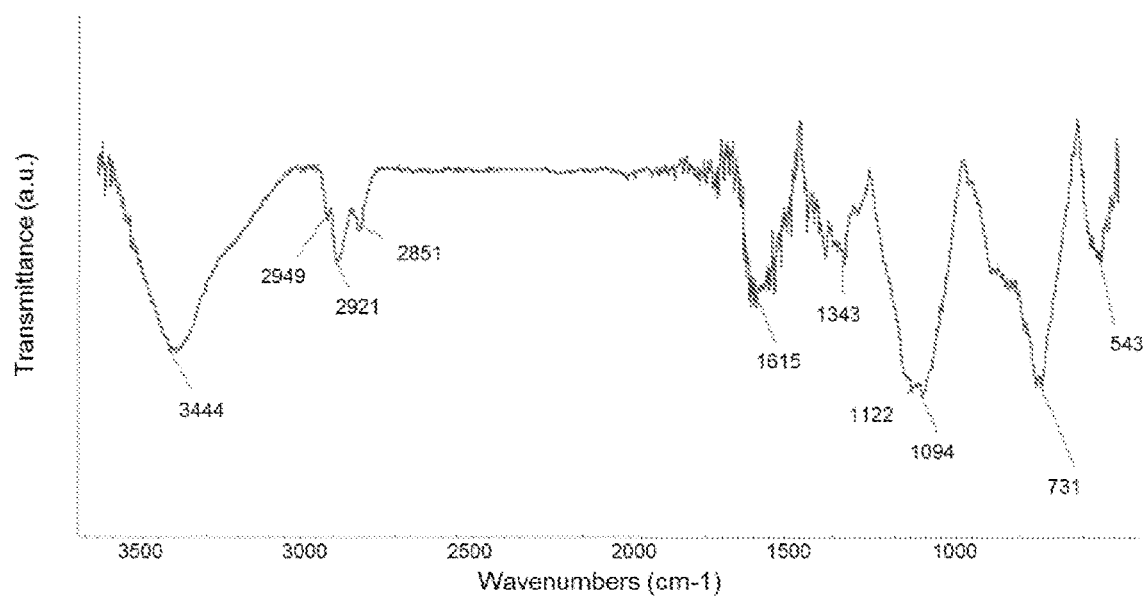
Fig. 5. FT-IR spectrum of the adduct of 1,6-bis(2,5-dimethyl-1*H*-pyrrol-1-yl)hexane with graphite

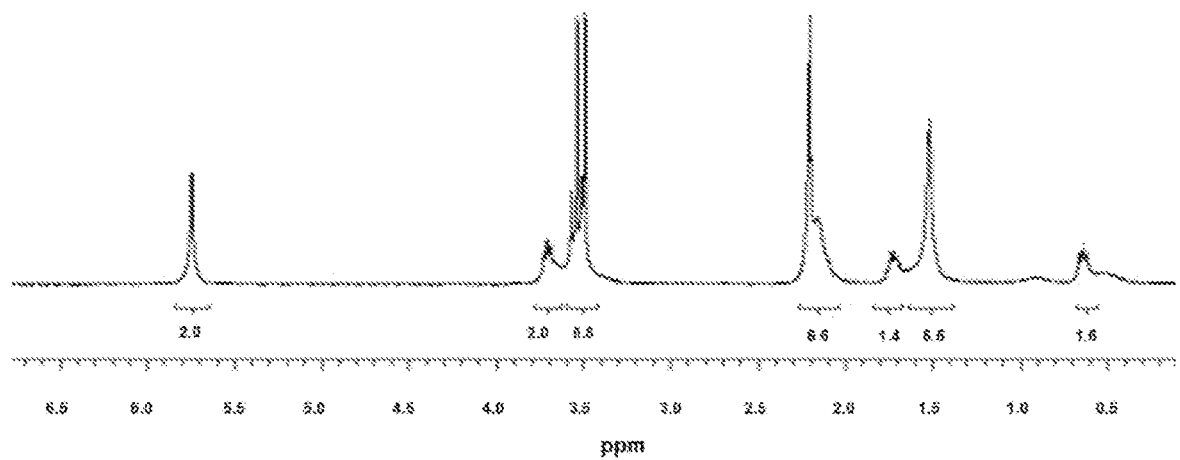
Fig. 6. $^1$H NMR spectrum, 400 MHz in CDCl$_3$, of 2,5-dimethyl-1-(3-(trimethoxysilyl)propyl)-1*H*-pyrrole

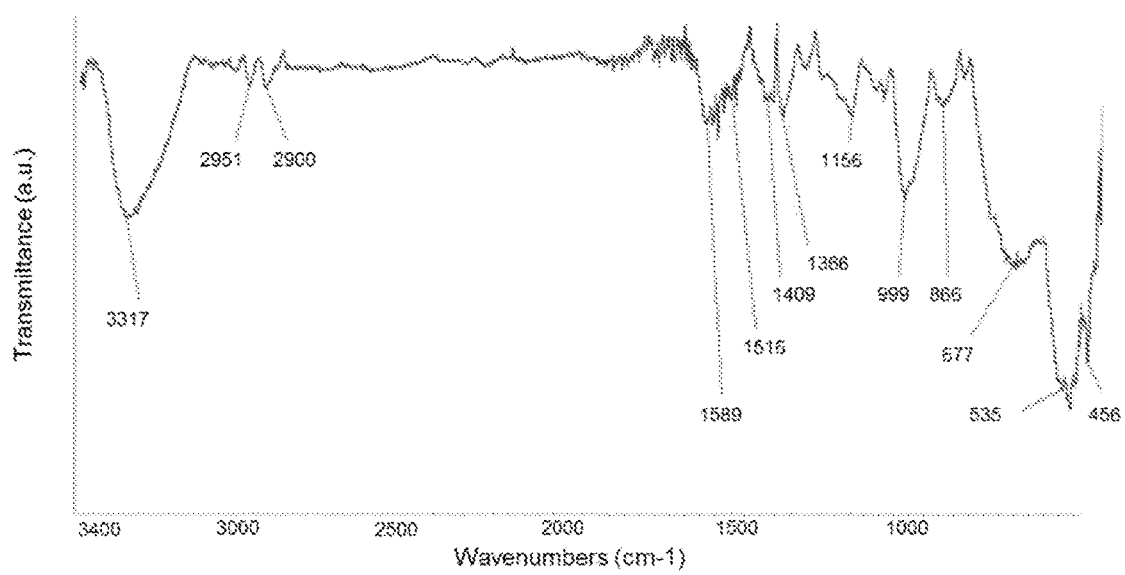
Fig. 7. FT-IR spectrum of the adduct of 2,5-dimethyl-1-(3-(trimethoxysilyl)propyl)-1*H*-pyrrole with graphite

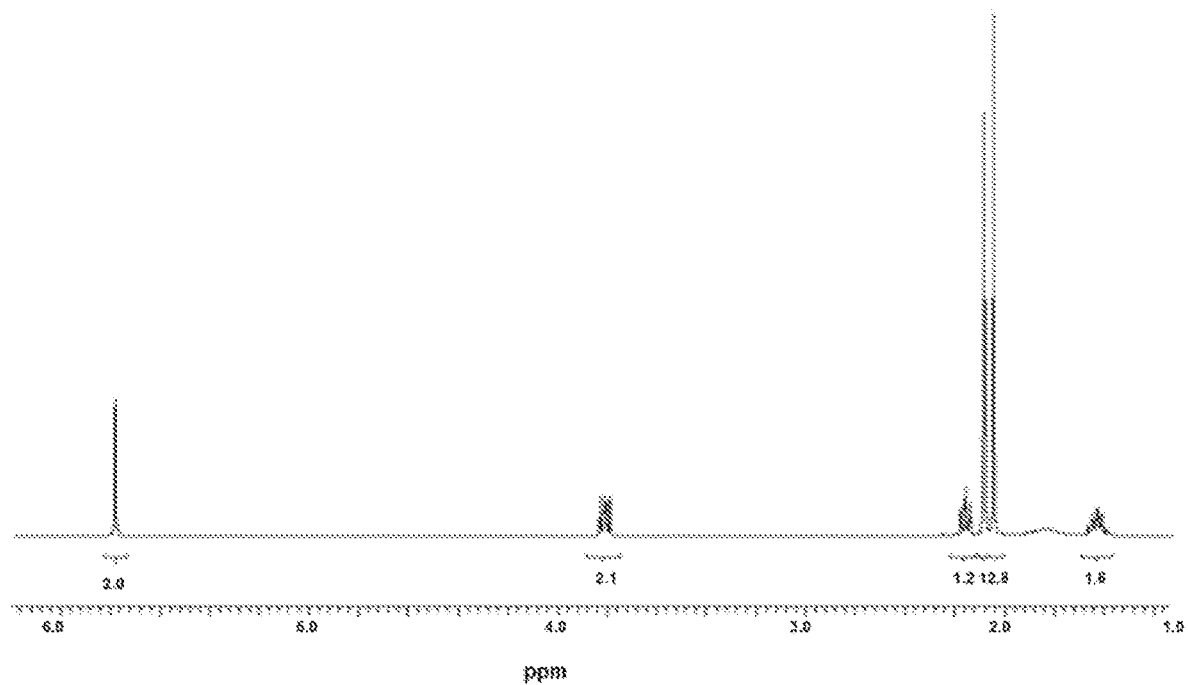
Fig. 8. ¹H NMR spectrum, 400 MHz in CDCl₃, of 3-(2,5-dimethyl-1H-pyrrol-1-yl)-1-dimethylpropan-1-amine

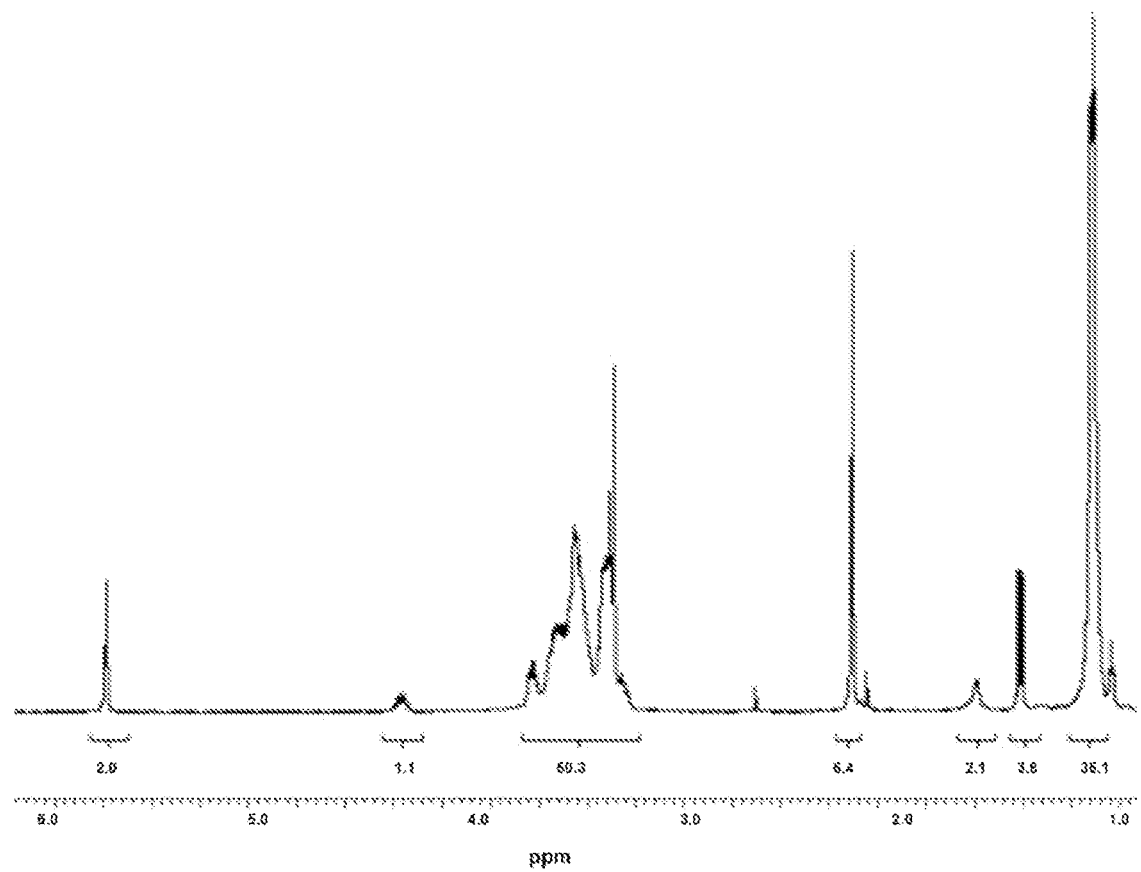
Fig. 9. ¹H NMR spectrum, 400 MHz in CDCl₃, of O-(2-(2,5-dimethylpyrrol-1-yl)propyl)-O'-(2-methoxyethyl)polypropylene glycol

ADDUCTS OF PYRROLE DERIVATIVES TO CARBON ALLOTROPES

This application is a national stage entry application under 35 U.S.C. § 371 based on International Application No. PCT/162017/057001, filed Nov. 9, 2017, and claims priority to Italian Patent Application No. 102016000113012, filed Nov. 9, 2016; the content of each application is incorporated herein by reference.

The present invention relates to adducts formed from carbon allotropes, wherein the carbon is $sp^2$ hybridized, for example carbon nanotubes, graphene or nanographites, carbon black, and from pyrrole derivatives in which the nitrogen atom bears substituents suitable for improving the physicochemical characteristics of said allotropes mainly by increasing their dispersibility and stability in organic liquid media and in organic polymer matrices, preferably of a lipophilic nature.

According to the definition in the Treccani encyclopaedia, lipophilic in chemistry describes substances, atoms, molecules etc. that dissolve easily in oils and fats. Thus, in a soap molecule, the hydrocarbon radical of the fatty acid is lipophilic, whereas the carboxyl group is hydrophilic-lipophilic.

Also according to the definition in the Treccani encyclopaedia, allotropy is the presence, in a chemical element, of forms that differ by a different arrangement of the atoms in the solid and hence by a different crystalline structure. It is known that numerous carbon allotropes exist. A first classification refers to the hybridization of the carbon atoms. In diamond, the carbon atoms are $sp^3$ hybridized. In other allotropes, the carbon atoms are $sp^2$ hybridized.

Among the allotropes with $sp^2$ hybridized carbon atoms, the following may be mentioned: graphene, nanographites consisting of a few graphene layers (from a few units to a few tens), graphite, fullerene, nanotoroids, nanocones, graphene nanoribbons, single-wall or multiwall carbon nanotubes, and carbon black, also called lampblack. Graphene is a layer of carbon atoms and therefore has the thickness of a carbon atom. Single-wall carbon nanotubes can be regarded as a rolled-up layer of graphene. Graphite, multiwall carbon nanotubes and carbon black are made up of graphene layers. Graphite consists of a variable number of graphene layers stacked into crystalline aggregates, with a typical spacing of about 0.34 nm. The number of stacked layers may be less than about ten, but may reach several thousand. Multiwall carbon nanotubes may be considered to be formed from several rolled-up graphene layers. As already stated, a single-wall nanotube is formed from one layer, and multi-wall nanotubes are formed from several layers. In each of these allotropes, rings are present as the base unit. These rings may typically have 5 or 6 carbon atoms. In these rings there are electrons present in $\pi$ orbitals, delocalized on the aromatic polycyclic system. This is possible because the rings are all condensed and constitute a single system. The simplest examples of polycondensed aromatic systems are the aromatic polycycles (including: pyrene, phenanthrene, anthracene). The carbon allotropes with $sp^2$ hybridized carbon constitute the equivalent of a polycondensed aromatic system with a different degree of planarity. For a system to be defined as aromatic, three conditions must be met: (a) the system must be cyclic, (b) the ring atoms must all have $sp^2$ hybridization and the sum of the $\pi$ electrons must satisfy Hückel's rule ($\pi=4n+2$, where n is an integer, including zero), (c) the system must be planar. All the requirements are met in the case of graphene. In the case of non-planar carbon allotropes, such as fullerene and carbon nanotubes, the curvature has an influence on the condition of planarity. However, such systems can be defined as aromatic, and represent an exception.

The carbon allotropes in which the carbon is $sp^2$ hybridized can be subdivided into "nano" and "nano-structured".

A chemical individual is defined as "nano" when it has at least one dimension under 100 nm. Carbon allotropes such as fullerene, carbon nanotubes, graphene and nanographites are so-called "nano" allotropes. Graphene is a layer of $sp^2$ hybridized carbon atoms, has the thickness of a carbon atom and therefore has a nanometric dimension. Carbon nanotubes have a diameter of a few nanometres. As noted above, graphite is formed from crystalline aggregates, which in their turn are formed from stacked graphene layers. When the number of stacked graphene layers is small, from less than ten to a few tens, the dimension of the crystalline aggregate in the direction orthogonal to the layers ranges from a few nm to a few tens of nanometres. These graphites are therefore called nanographites. The individual tubes can be separated from the tangle in which they are intertwined. It is also possible to perform exfoliation of a graphite having various initial numbers of stacked layers, obtaining nanographites with a small number of stacked layers, as well as graphene.

In contrast, carbon black, which has been used for more than a century for reinforcing polymer materials and for many other applications, is "nano-structured". In fact it consists of fundamental particles that have nanometric dimensions, combined to form aggregates in which these fundamental particles are held together by covalent bonds. These aggregates are larger than 100 nm. The thermomechanical stresses typical of the action of mixing carbon black with polymer matrices and typical also of the use of said matrices are not able to separate the aggregates into the fundamental components. Aggregation leads to the creation of voids between the fundamental particles, creating a particular structure for carbon black. The larger the quantity of voids, the larger the structure. The definition of nano-structured filler is derived from this. The aggregates are thus united by van der Waals forces to create agglomerates, which can, however, be separated into the initial aggregates by thermomechanical stresses.

The carbon allotropes in which carbon is $sp^2$ hybridized, such as carbon nanotubes, graphene, graphite and carbon black, possess electrical and thermal conductivity. In particular, carbon nanotubes and graphene possess exceptional mechanical properties and electrical and thermal conductivity. They have nanometric dimensions, of a few nanometres: one dimension, in the case of graphene, and two dimensions in the case of nanotubes. The nanometric size and the particular geometry, lamellar in the case of graphene, tubular in the case of nanotubes, gives them a high surface area and thus the capacity to establish a large interfacial area with the matrix in which they are incorporated, greatly influencing their properties. Owing to their properties, carbon allotropes are used both in polymer, plastic or elastomeric matrices, and in liquid media that will then form coating layers. They promote mechanical reinforcement, thermal and electrical conductivity of the materials in which they are incorporated.

Among carbon allotropes based on $sp^2$ carbon atoms, carbon black is by far the most used. It is sufficient to think of its use in elastomeric and thermoplastic matrices, in coating layers, and in toners. Carbon black provides mechanical reinforcement, electrical conductivity, protection against ultraviolet radiation, as well as colouring of the end product.

There has been much research into "nano" carbon allotropes, for example nanographites consisting of a few graphene layers (from a few units to some tens) and single-wall or multiwall carbon nanotubes, and carbon black. Both these allotropes, and especially nanotubes, find industrial application. There is enormous interest in graphene, but its meager availability makes it a product that is still very little used industrially. The improvement in the aforementioned properties is particularly great when the "nano" carbon allotropes are used, such as carbon nanotubes, graphene and nanographites. Moreover, these allotropes have a notable flame-retardant effect in polymer matrices.

In the case of polymer matrices, the carbon allotropes can be mixed directly in said matrices, forming the finished product by the traditional technologies of mixing, or they may form part of predispersions, typically in concentrations greater than those employed in the final product. Similarly, in the case of dispersions in liquid media, the carbon allotropes may form part of the final formulation, to be used for example for forming coating layers, or may be present in a "stock dispersion", to be used for preparing various formulations.

For all the aforementioned compositions that contain carbon allotropes, the aim is to obtain optimum distribution and dispersion of the allotropes. In the case of dispersions in liquid media, the aim is firstly to obtain stability of the dispersion itself, avoiding sedimentation of the allotrope. The instability of these dispersions accounts for the lack of development for applications on an industrial scale. Such problems have been encountered in particular for the "nano" carbon allotropes. In the case of polymer composites the aim is in particular to ensure optimum interaction of the allotropes with the matrix, and stable interaction in the conditions of use of the material. In fact, the main problems that may be encountered in the case of polymer composites containing carbon allotropes is insufficient interaction of said allotropes with the polymer matrix. Such problems have been encountered in particular for "nano" carbon allotropes. This results in an insufficient transfer of the properties of the allotropes to the composite material and leads to instability of the dispersion of the allotropes themselves, which tend to form aggregates, with notable impairment of the properties of the final material.

The main objective in the preparation of composites containing $sp^2$ hybridized carbon allotropes is thus to obtain optimum dispersion of the allotropes. It would be desirable to identify a criterion that makes it possible to obtain said optimum dispersion.

The article by Bergin et al., ACS Nano 2009, Vol. 3(8) p. 2340, gives the dispersibility of single-wall carbon nanotubes in various kinds of solvents. These solvents are: N-methyl-2-pyrrolidone, 1,3-dimethyl-2-imidazolidinone, N-vinylpyrrolidone, N-dimethylacetamide, N-dimethylformamide, 1-cyclohexylpyrrolidone, N-butyl-2-pyrrolidone, N-ethyl-2-pyrrolidone, 1-benzyl-2-pyrrolidinone, dimethyltetrahydro-2-pyrimidinone, oxo-pyrrolidine propionitrile, N-octylpyrrolidone, N-dodecylpyrrolidone and N-formylpiperidine. The dispersibility of the nanotubes is measured by determining their concentration in the dispersion after centrifugation. The article gives the dependence of the dispersibility of the nanotubes on the solubility parameter (the authors report better dependence on the solubility parameter derived from values of surface energy rather than from values of cohesive energy) of the medium in which they are dispersed. The points that describe this dependence are located around a straight line that has a non-negligible slope. This signifies that even small variations of the solubility parameter of the matrix may lead to notable differences in the dispersibility of the nanotubes. The article also reports some exceptions, suggesting the need for further research.

However, good agreement between the solubility parameter of the carbon nanotubes and the solubility parameter of the medium in which they are dispersed is still a preferred reference point for obtaining good dispersibility of carbon nanotubes. In fact, in the article Scientific Reports (2014), 4:7232, nine different polymer matrices are used. They are: poly(styrene-co-butadiene) (known in the field of elastomers as SBR), poly(1,4-cis-butadiene), poly(1,4-cis-isoprene), poly(butadiene-co-acrylonitrile) (known in the field of elastomers as NBR), poly(ethylene-co-1-butene-co-acrylonitrile) (or hydrogenated poly(butadiene-co-acrylonitrile)) (known in the field of elastomers as hydrogenated nitrile rubber), poly(ethylene oxide-co-epichlorohydrin-allyl glycidyl ether), poly(ethylene-acrylic monomer) (known in the field of elastomers as acrylic elastomers or ACM), poly(vinylidenefluoride-co-tetrafluoroethylene-co-hexafluoropropylene) (known in the field of elastomers as fluorine rubber). In the work it is demonstrated experimentally that agreement between the solubility parameter of the matrix and that of the nanotubes is important to allow formation of a continuous network of nanotubes in said matrix and thus obtain electrical conductivity. In fact curves are presented that correlate the electrical conductivity with the solubility parameter of the matrix. It is reported that the best dispersion is obtained with fluorine rubber as the matrix. It is important to note that composites containing nanotubes display varying values of electrical conductivity even though there is little variation in the values of the solubility parameters of the matrix.

Thus, the works in the literature demonstrate that if we wish to achieve good dispersibility of carbon nanotubes in a medium or in a matrix, it is important to have solubility parameters that are similar for the nanotubes and for the medium or matrix. To achieve optimum dispersibility of the nanotubes it is necessary to have particular values of the solubility parameter of the matrix. A very interesting observation is that to obtain better dispersion of carbon nanotubes in a polymer matrix, regardless of the solubility parameter of said matrix, it is possible to add a nanotube compatibilizer. Still in the article Scientific Reports (2014), 4:7232, it is reported that the addition of small amounts of fluorine rubber, as polymeric compatibilizer of the nanotubes, leads to improved dispersion of them and higher electrical conductivity.

It is clear that the carbon allotropes are lipophilic. From this, and from what has been said above, it is also clear that, in principle, good dispersion of carbon allotropes can be achieved in lipophilic media. Regarding carbon nanotubes as allotropes, it should be emphasized that carbon nanotubes are made up of nanofibres, entangled together to form balls. When we speak of dispersion, we mean that the nanotubes must be disentangled from the ball and dispersed individually. To achieve this, it is not just a matter of using a lipophilic medium—it is necessary to optimize the nature of the dispersing lipophilic medium.

Obtaining optimum dispersion of the carbon allotropes in a lipophilic matrix and particularly in a lipophilic polymer matrix is a fundamental objective with a view to their industrial development. In fact, the polymers that are by far the most important on an industrial scale are of a lipophilic nature. As an example, we may mention: poly(ethylene), poly(propylene), poly(styrene), poly(butene), poly(isoprene), poly(butadiene), poly(ethylene-co-propylene), poly(isobutene).

In the prior art there are many examples of composites based on a lipophilic matrix, containing carbon allotropes of nanometric size. Some examples of such composites containing "nano" allotropes are presented below.

Composites based on carbon nanotubes are described in "Carbon nanotube-polymer interactions in nanocomposites: A review, Composites Science and Technology 72 (2011) 72-84". Composites based on graphene and nanographites are described in "Graphene-based polymer nanocomposites." Polymer, 52(1), 5-25 (2011). Dispersions of carbon nanotubes in elastomer matrices are described in "Multiwall carbon nanotube elastomeric composites: a review" Polymer, 48(17), 4907-4920 (2007) and in "The Role of CNTs in Promoting Hybrid Filler Networking and Synergism with Carbon Black in Mechanical Behavior of Filled Polyisoprene" *Macromol. Mater. Eng.*, 298, 241-251 (2012). Dispersions of nanographites in elastomer matrices are reported in "Filler Networking of a Nanographite with a High Shape Anisotropy and Synergism with Carbon Black in Poly(1,4-Cis-Isoprene)-Based Nanocomposites" Rubber Chemistry and Technology, Vol. 87, No. 2, pp. 197-218 (2014).

However, all these composites have both carbon allotropes dispersed at the level of the single constituent particles, or at the level of the single nanotubes or of single lamellae of graphene or of aggregates with a few graphene layers, and agglomerates. In particular, in "Filler Networking of a Nanographite with a High Shape Anisotropy and Synergism with Carbon Black in Poly(1,4-Cis-Isoprene)-Based Nanocomposites" Rubber Chemistry and Technology, Vol. 87, No. 2, pp. 197-218 (2014), it is shown that the nanographite aggregates tend to form aggregates formed from several graphene layers stacked in crystalline structures when they are incorporated in the crosslinked elastomer composite. The problem of dispersion of carbon allotropes of nanometric dimensions in lipophilic matrices at the level of the constituent particles, whether the layer of graphene or the single nanotube, has not yet been solved, at least not completely and in a controlled manner.

In the prior art, various methods are presented for dispersing the "nano" carbon allotropes in lipophilic matrices.

In "The Role of CNTs in Promoting Hybrid Filler Networking and Synergism with Carbon Black in the Mechanical Behavior of Filled Polyisoprene" *Macromol. Mater. Eng.*, 298, 241-251 (2012), the nanotubes are mixed with rubber in an internal mixer, utilizing the thermomechanical energy of mixing, without any preliminary chemical modification. This leads to fracture of the nanotubes, which are shown to have a smaller length than the nanotubes before mixing.

In the article Carbon 2012, 50, 4685-4695, nanotubes are mixed with natural rubber in natural rubber latex, modifying the nanotubes with a surfactant such as sodium dodecyl sulphate. However, this method necessitates having a latex of a polymer, and preparing aqueous dispersions, and so is a method that may have limited applications.

In the article Journal of Applied Polymer Science 2012, 125, E76-E84, mixing with natural rubber is carried out with the aid of a solvent such as toluene. Apart from the use of an aromatic solvent, which is undesirable, it is obvious that it is complex to use a solvent, and this seems to rule out any industrial development.

Moreover, it is known that the solubility of polymers in a solvent depends on their molecular weight and on their degree of stereoregularity. It is known that polymers of low molecular weight become soluble in solvents in which the same polymers, of high molecular weight, are not soluble. Moreover, polymers with the same repeating unit but with a different degree of stereoregularity may or may not be soluble in the same solvent. An example is polystyrene. Atactic polystyrene is soluble in a ketone such as methyl ethyl ketone, whereas isotactic polystyrene and syndiotactic polystyrene are not soluble in methyl ethyl ketone. Isotactic polypropylene is not soluble in boiling heptane, whereas atactic polypropylene is soluble in boiling heptane. Thus, wishing to follow the route of dispersing carbon allotropes in a lipophilic matrix using solvents, we might think, in principle, of dispersing the carbon allotropes in solvents that have the capacity to dissolve polymers of low molecular weight and/or having a low degree of stereoregularity. These solvents, although clearly being organic molecules, also contain polar groups. Typical examples are: alcohols such as isopropanol and butanol, ketones such as acetone and methyl ethyl ketone, and esters such as ethyl acetate. These substances are less critical from the viewpoint of effects on health and the environment, for example relative to toluene. By mixing with solvent, masterbatches might be prepared containing the carbon allotrope in the polymer matrix. These masterbatches might then be dispersed in matrices of high molecular weight polymers. A condition for carrying out this procedure is good dispersion of the $sp^2$ hybridized carbon allotrope in said solvent.

In the article Compos. Sci. Technol. 100 (0) (2014) 143 and 151 and in the article Macromolecules 2012, 45, 6045-6055 the starting point is graphene oxide, which is reduced with hydrazine. Then it is mixed with natural rubber latex and finally undergoes coagulation. Obviously this method involves a chemical reaction such as oxidation of graphite to graphite oxide, a reaction that takes place in harsh conditions, with strong acids and powerful oxidants, and that has some level of hazardousness. This reaction leads to extensive modification of the hybridization of the carbon atoms. Moreover, it requires a reaction of reduction with a toxic ingredient such as hydrazine. Finally, as already mentioned, it requires the presence of polymer latices.

In the article Compos. Sci. Technol. 74 (0) (2013) 166 and 172, graphite oxide is first expanded thermally and then reduced, again with hydrazine, to obtain graphene or aggregates with a few graphene layers. Once again, the complexity of the method is obvious.

The prior art is very rich in data and experiments on the dispersibility of carbon black in lipophilic polymer matrices, as already reported in Carbon Black 2nd Edition edited by J. B. Donnet, R. C. Bansal, M. J. Wang, Marcel Dekker Inc., 1993. A large volume of carbon black is used in elastomer matrices. It is known that elastomers cannot find practical applications not only if they have not been vulcanized, but also if they have not been reinforced by adding reinforcing fillers. Carbon black has been the reference carbon allotrope for reinforcing elastomers for more than a century. In fact, carbon black has sub-micrometric dimensions of its constituent particles and preferably also has aggregates of said particles, is not soluble in the elastomer matrix and has a significantly higher modulus than that of the matrix itself. Therefore it can act as reinforcement of the elastomer matrix. The sub-micrometric size makes it possible to have a sufficient surface area for exerting reinforcing action. The surface area of the filler is in fact transformed into the interfacial area with the polymer matrix. The interfacial area is in fact given by the product of the surface area and the density of the filler and its volume fraction. An extensive interface and good interaction between the reinforcing filler and the polymer chains are thus prerequisites for mechanical reinforcement since they allow transfer of stress to the polymer matrix, which is able to store energy. It is therefore clear that the "nano-fillers" and the "nano" carbon allotropes mentioned at the beginning of the text have great potential, on account of their nano-dimensions and thus large surface area and large interfacial area. Among the applications of elastomer matrices containing carbon black, it is appropriate to mention the application in tyre compounds. Mixing of carbon black with elastomers is performed by means of thermomechanical stress. This mixing is undoubtedly sufficient for application of the compounds for tyres. Nevertheless, the degree of dispersion is still not optimal, as is discussed hereunder.

In fact, in the case of application for tyre compounds, the ideal situation is to obtain the desired mechanical reinforcement with limited dissipation of energy. The theory of reinforcement, for example described by Donnet, J. B., Custodero, E., 2005. Reinforcement of elastomers by particulate fillers, in: Mark, J. E., Erman, B., Eirich, F. R. (Eds.), The Science and Technology of Rubber, third ed. Academic Press, San Diego, pp. 367-400, teaches that the surface area is responsible for the mechanical reinforcement at low strains. In fact, a high surface area promotes extensive interaction with the polymer chains and with other filler particles, an interaction that is based essentially on non-bonding forces, typically van der Waals forces. To achieve effective action of reinforcement of an elastomer matrix, the fillers must be used in large amounts. Typically, the ASTM standard compounds require the use of more than 30 parts of filler per 100 parts of elastomer. With this amount of filler, the filler is above its percolation threshold, i.e. it forms a network. Therefore there are not only filler-polymer interactions but also filler-filler interactions. These interactions are promoted by a high surface area. Applying energy to the composite material that contains the reinforcing fillers and gradually increasing the amplitude of the strain, the reinforcement based on non-bonding interactions is reduced. There is thus a reduction of the viscoelastic modulus, according to a phenomenon known as the Payne effect. When an elastomer composite is subjected to high strains it is nevertheless subject to the reinforcing action of the reinforcing fillers. The reinforcing action at high strains is due to the stable interaction between the polymer matrix and the filler, which is due to the aforementioned structure of the filler, i.e. the voids between the fundamental particles of said filler, which are able to receive the polymer chains, anchoring them and transforming them from a viscous fluid into a reinforcing filler. In the applications of elastomer compounds in tyres, it would thus be ideal to maintain the stable reinforcement typical of the high strains and to reduce the reinforcement at low strains which is removed by applying energy to the elastomer composite. That is, it would be ideal to reduce the Payne effect. In fact, this energy is dissipated to overcome the non-bonding interactions. For application in tyre compounds, this is reflected in fuel consumption and in increased environmental impact. Reduction of the Payne effect passes through optimization of the dispersion of the carbon allotrope, separating its aggregates and/or the elementary particles, and covering them with a layer of elastomer. This objective has not yet been achieved in the field of elastomer compounds and, in particular, in the field of tyres. At present, better distribution and dispersion can only be achieved with a higher energy of mixing, but this leads to degradation of the polymer matrix. It would therefore be desirable to find a means of modifying carbon allotropes that allows better dispersion thereof in the elastomer matrix.

Modifications of carbon allotropes that promote their dispersibility in lipophilic matrices are reported in the literature.

US 2006/0045838 describes adducts between carbon nanotubes and soluble polymers selected from poly(thiophene), poly(pyrrole), poly(fluorene), poly(phenylene), poly(phenylene ethynylene), poly(phenylene vinylene), poly(alkylidene fluorene), poly(fluorene bithiophene) and combinations thereof. The lipophilic nature of the modifier promotes dispersibility in aromatic solvents such as chloroform. These modifiers are of a polymeric nature. Therefore it is first necessary to synthesize the polymer. The adduct with the carbon nanotube must therefore be produced by dissolving in a solvent, also not ideal from the viewpoint of environmental impact, such as chloroform. It is obvious that this approach is not applicable to the industrial production of elastomer goods.

The review Chem. Soc. Rev., (2009), 38, 2214-2230 reports the methods of organic functionalization of (single-wall) nanotubes. They are subdivided into: (i) formation of amides and esters on functionalized nanotubes and (ii) addition reactions. The first method requires firstly oxidation of the nanotubes with introduction of carboxyl groups. As already mentioned, this reaction requires harsh conditions, with strong acids and powerful oxidants, and it has some level of hazardousness. It is difficult to imagine its large-scale industrial development. Moreover, oxidation must be followed by further chemical reactions. This approach therefore seems feasible in suitably equipped chemical laboratories. It certainly cannot be carried out in situ in processing equipment. The addition reactions (second method) entail fluorination with elemental fluorine, the addition of carbenes by functionalization with octadecylamine followed by the addition of phenyl(bromodichloromethyl)mercury as the source of dichlorocarbene, the addition of nitrenes using alkyl azidoformates, 1,3-dipolar cycloadditions, nucleophilic additions that lead for example to cyclopropanation using diethyl bromomalonate and 1,8-diazabicyclo[5.4.0] undecene, the direct addition using radicals, and direct arylation using diazonium salts. All these methods entail the use of chemical reactions, sometimes to be performed on the functionalized nanotube. The equipment to be employed and the typical conditions of the chemical reactions are obvious. They seem to be typical approaches for preparing small samples. Sometimes it is necessary to use chemicals that are critical from the viewpoint of effects on health. Finally, carrying out these reactions in situ, in machines intended for mixing, cannot be imagined. In this review, the use of modifiers that react with the carbon nanotubes by a Diels-Alder reaction is discouraged, bearing in mind that the reverse Diels-Alder reaction, which leads to destruction of the adduct, can easily take place merely by heating the adduct itself.

It is important to note that every route selected for modification of the carbon allotropes is characterized by a certain type of "modification chemistry", which involves a certain class of functional groups.

It would be desirable to be able to prepare stable dispersions of carbon allotropes with $sp^2$ hybridized carbon atoms both in liquid media and in polymer matrices of a lipophilic nature, especially in polymer matrices of a lipophilic nature.

It would be desirable to have at our disposal dispersions between pyrrole derivatives and $sp^2$ hybridized carbon allotropes in which said dispersions are obtained by modification of the carbon allotropes that leaves their $sp^2$ nature substantially unchanged.

It would moreover be desirable for this modification to take place in a simple manner, and by performing the modification reaction by feeding the reagents onto the allotrope itself and carrying out the modification reaction in situ, that is in the polymer matrix itself.

It would also be desirable to be able to use simple techniques and with reduced environmental impact for carrying out the modification reactions. In the case of dispersions in polymer matrices, it would be desirable to avoid the use of any solvent.

It would therefore be desirable to perform modifications of the carbon allotropes with compounds that contain functional groups that are able to interact with the aromatic rings of the carbon allotropes, by carrying out non-bonding or supramolecular interactions or by forming covalent bonds that, however, at the same time do not substantially modify the electronic nature of the allotrope that has been modified.

It would be desirable to be able to use, for modifying the carbon allotrope, a compound that contains the functional group that promotes interaction with the carbon allotrope but also another or other functional groups that promote interaction with the polymer matrix.

It would be desirable for the family of compounds that form the adducts with the carbon allotropes to be characterized by just one type of functional group that promotes interaction with the carbon allotrope, it thus being possible to carry out a reproducible interaction between the compound and the allotrope, and by various types of functional groups that promote interaction with liquid media or polymer matrices, thus making it also possible to prepare stable dispersions in liquids and matrices of a lipophilic nature, optimizing the interaction with the lipophilic matrix.

It would also be desirable if, among the functional groups that promote favourable interaction of the carbon allotropes with liquid media or polymer matrices, there are also functional groups that are able to promote favourable interaction with solvents consisting of organic molecules but also containing polar groups, so as to be able to use a very large number of solvents as well as for the purpose of extending the possibility of compatibilization of the carbon allotropes.

It would also be desirable to have an extremely versatile method for modifying the carbon allotropes, for example enabling the reagents that form the compound that will modify the allotrope to be fed onto the allotrope itself. Thus, it would be desirable to be able to perform both the synthesis of the modifier and, of course, the subsequent modification, on the allotrope.

It would finally be desirable that the adducts formed from the allotrope and the modifier should make it possible to obtain stable dispersions of carbon allotropes, in order to maintain their characteristics over time.

One aim of the present invention is therefore to provide modification of a carbon allotrope in which the carbon is $sp^2$ hybridized by introducing at least one lipophilic substituent, improving the dispersibility of the carbon allotrope in lipophilic media.

One aim of the present invention is therefore to provide stable adducts between a carbon allotrope in which the carbon is $sp^2$ hybridized and at least one compound containing functional groups able to interact with the aromatic rings of the carbon allotropes and functional groups that improve the dispersibility of the allotrope in lipophilic media and matrices.

One aim of the present invention is to form a stable adduct between a carbon allotrope and a compound as described above without substantially altering the hybridization of the carbon atoms of the allotropes and thus without substantially altering their properties.

One aim of the present invention is therefore to provide stable adducts between a carbon allotrope in which the carbon is $sp^2$ hybridized starting from simple, readily available chemicals.

One aim of the present invention is to use, for forming the adduct, a family of compounds that use the same experimental conditions for forming the adduct and at the same time make it possible to modulate the chemical nature of the modified allotrope.

One aim of the present invention is to carry out the reaction between the compound and the carbon allotrope in a simple and reproducible manner, with simple experimental conditions, according to the principles of green chemistry, therefore using simple techniques with reduced environmental impact.

An important aim of the present invention is to carry out the reaction for forming the compound that will form the adduct with the carbon allotrope on the allotrope itself, thus eliminating a basic step of the process, i.e. that of the synthesis and isolation of the compound.

These and other aims of the present invention are achieved by means of an adduct of a compound of formula (I)

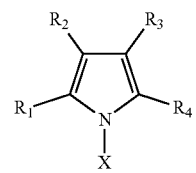

in which $R_1$, $R_2$, $R_3$, $R_4$ are selected independently from the group consisting of: hydrogen, $C_1$-$C_3$ alkyl, linear or branched $C_2$-$C_{18}$ alkenyl or alkynyl, aryl, linear or branched $C_1$-$C_{18}$ alkyl-aryl, linear or branched $C_2$-$C_{18}$ alkenyl-aryl, linear or branched $C_2$-$C_{18}$ alkynyl-aryl, heteroaryl, and X is selected from the group consisting of:

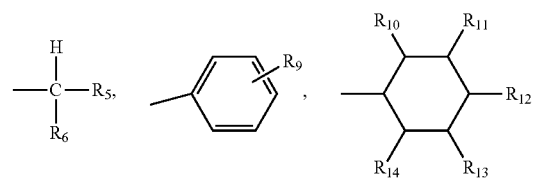

in which $R_5$ and $R_6$ are selected independently from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, or $R_5$ or $R_6$ are each or both

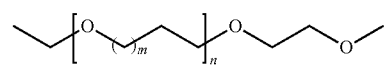

where m=0, 1, 2 and n=1-30 where if only one of $R_5$ or $R_6$ is

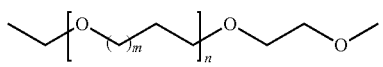

where m=0, 1, 2 and n=1-30
then the other one is selected from the group consisting of:
hydrogen, $C_1$-$C_{18}$ alkyl, linear or branched $C_2$-$C_{18}$ alkenyl or alkynyl;
or $R_5$ and/or $R_6$ are:

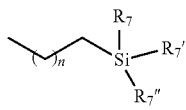

where n=0, 1, 2, 3
and $R_7$, $R_7'$, $R_7''$ are selected independently from the group consisting of: $C_1$-$C_4$ alkyl; $C_1$-$C_4$ oxygen-alkyl
or $R_5$ and/or $R_6$ are:

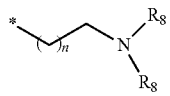

where n=0, 1, 2, 3
and $R_8$ is selected from the group consisting of: $C_1$-$C_4$ alkyl;
or $R_5$ and/or $R_6$ are:

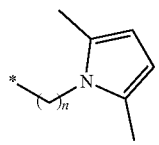

where n is an integer between 1 and 10
$R_9$ is selected from the group consisting of: hydrogen, alkyl, aryl, benzyl, amine, alkylamine, arylamine, benzylamine, aminoaryl;
$R_{10}$, $R_{11}$, $R_{12}$, $R_{13}$ and $R_{14}$ are selected independently from the group consisting of: hydrogen, $C_1$-$C_{18}$ alkyl, linear or branched $C_2$-$C_{18}$ alkenyl or alkynyl, 1-(4-aminocyclohexyl)methylene
and a carbon allotrope that contains $sp^2$ hybridized carbon atoms.

In this way, an adduct is obtained containing carbon allotropes with $sp^2$ hybridized carbon atoms, which is dispersible in numerous matrices of a lipophilic nature, and can be used in processes where it is necessary to maintain the characteristics of said allotropes.

Preferably said $R_1$, $R_2$, $R_3$, and $R_4$ are selected independently from the group consisting of: H, $CH_3$, $CH_2CH_3$, phenyl.

Preferably the carbon allotrope or its derivative are selected from the group consisting of: carbon black, fullerene, single-wall or multiwall carbon nanotubes, graphene, graphite with a number of graphene layers between 2 and 10000.

Preferably said carbon allotrope derivative contains functional groups, selected from the group consisting of:
oxygenated functional groups, preferably hydroxyls, epoxides;
functional groups containing carbonyls, preferably aldehydes, ketones, carboxylic acids;
functional groups containing nitrogen atoms, preferably amines, amides, nitriles, diazonium salts, imines;
functional groups containing sulphur atoms, preferably sulphides, disulphides, mercaptans, sulphones, sulphinic and sulphonic groups.

Preferably the carbon allotrope derivative is graphite oxide or graphene oxide.

We thus have a wide range of carbon allotropes that contain $sp^2$ hybridized carbon atoms at our disposal.

A further aim of the present invention is to provide a process for preparing an adduct according to one or more of the preceding claims comprising the steps of:
i. providing a solution of a compound of formula (I) in a protic or aprotic polar solvent;
ii. providing a suspension of the carbon allotrope in the protic or aprotic polar solvent used for preparing the solution referred to in step i.;
iii. mixing said solution and said suspension;
iv. removing said solvent from the mixture obtained in step iii.;
v. supplying thermal and/or mechanical energy and/or photon irradiation energy to the mixture obtained.

Preferably the thermal energy is supplied at a temperature between 50° C. and 180° C. for a time between 15 and 360 minutes.

Preferably the mechanical energy is supplied for a time between 15 and 360 minutes.

Preferably the photon irradiation energy is supplied at a wavelength between 200 and 380 nm for a time between 30 and 180 minutes.

The method of preparation of the adduct according to the present invention, starting with the synthesis of the starting monomers, is described hereunder.

According to the present invention the compositions described were obtained by synthesizing the compound of formula (I) starting from a primary amine of general formula

R—$NH_2$ in which R is selected from the group consisting of: hydrogen, $C_1$-$C_3$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl.

These primary amines are largely commercially available or may be prepared according to the classic techniques for preparing the primary amines. [T W Graham Solomons, Craig B Fryhle; *Chimica organica*, 2008, Zanichelli]

To obtain the compound of formula (I), the primary amine is reacted with a diketone of general formula

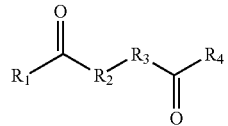

in which $R_1$, $R_2$, $R_3$, $R_4$ are selected independently from the group consisting of: hydrogen, $C_1$-$C_{22}$ alkyl, linear or branched $C_2$-$C_{22}$ alkenyl or alkynyl, aryl, $C_1$-$C_{22}$ alkyl-aryl, linear or branched $C_2$-$C_{22}$ alkenyl-aryl, $C_2$-$C_{22}$ alkynyl-aryl, heteroaryl.

As an example, the preparation of a pyrrole derivative of formula (I), namely 1-hexyl-2,5-dimethyl-1H-pyrrole, by a two-step process is described hereunder.

1-Hexylamine is reacted with 2,5-hexanedione in equimolar amounts, in the absence of solvents and without adding catalysts, for a reaction time equal to about 5 hours, at temperatures above 100° C., preferably 150° C., obtaining 1-hexyl-2,5-dimethyl-1H-pyrrole with high yields, equal to about 95%.

The carbon allotropes according to the present invention are more or less reactive aromatic systems, and are therefore subject to various types of intermolecular interaction.

These include stacking. In fact, stacking is defined as a stacked arrangement of aromatic molecules. Molecules containing aromatic rings in fact tend to assume a stacked arrangement on one another spontaneously. This is the origin of the concept of aromatic interaction (or π-π interaction), which means a bond of the non-covalent type that is established between organic compounds containing aromatic groups, on account of intermolecular superposition of the p orbital in π-conjugated systems. This type of interaction makes the bond even more stable, since it increases the number of π electrons.

The carbon allotropes may also give rise to the formation of covalent bonds, through various types of chemical reactions, such as those presented in the review, Chem. Soc. Rev., (2009), 38, 2214-2230.

According to the present invention, compositions are produced in which there are stable interactions between the carbon allotropes and pyrrole derivatives bearing lipophilic substituents on the nitrogen atom. The 5-membered heterocyclic rings, such as pyrrole, are termed "electron-rich" because the aromatic ring consists of 5 atoms and 6 π electrons. The electron density per atom is therefore greater than for a benzene ring. Their pentagonal structure and the presence of the heteroatom make the system less stable, which is therefore far more reactive compared to benzene. It is known that of the three electron-rich heterocycles, pyrrole is mid-way in terms of reactivity relative to furan and thiophene. The electron-rich heterocycles are less reactive than the dienes but more reactive than benzene. They are in fact able to give reactions typical of the electron-rich dienes.

According to the present invention the term adduct means a compound obtained by an interaction/reaction that might lead both to the formation of supramolecular compounds, i.e. in which the starting chemical individuals interact through non-bonding interactions, and compounds containing covalent bonds.

In the reaction that leads to the formation of the adduct, the following two types of interaction/reaction may be presumed:
  (i) π-π interaction. This form of interaction may occur between systems that possess π electrons, and therefore have $sp^2$ or sp hybridization. The interaction is between a doublet of π electrons and a σ orbital, or between the electrons of a σ orbital and a π orbital, or between the electrons of two π orbitals. This type of adduct is also known as a "π complex". As noted above, this type of interaction leads to stacking.
  (ii) a reaction that leads to the formation of covalent bonds between the pyrrole ring and the carbon allotrope. A typical reaction is a reaction of cyclo-addition such as the Diels-Alder reaction, which may take place between the aromatic rings of the graphitic compound and the compound containing the pyrrole ring or a compound thereof derived from that containing the pyrrole ring. This last-mentioned derivative might form in the conditions of interaction with the carbon allotrope, especially temperature and time.

The allotrope itself may play an important role in the type of interaction/reaction between the pyrrole compound and the graphitic carbon allotrope. In fact the catalytic action of graphites, nanographites and derivatives such as graphite oxides and graphene oxides is known. Articles in the scientific literature that describe this catalytic behaviour are for example Navalon, Sergio, et al. "Carbocatalysis by graphene-based materials." *Chemical reviews*, 114.12 (2014): 6179-6212.

As mentioned above, the carbon allotropes, in particular the "nano" allotropes such as fullerene, carbon nanotubes, graphene and nanographite, may contain various kinds of functional groups. According to the present invention, the addition reaction is performed between molecules with a pyrrole ring bearing a lipophilic substituent on the nitrogen atom. Formation of the adduct may take place through functional groups present on the lipophilic substituent and functional groups present on the carbon allotrope.

According to the present invention, the adduct that forms by an addition reaction between the carbon allotrope and the pyrrole compound bearing a lipophilic substituent on the nitrogen atom may be reversible. Reversibility of the adduct may be a function of various reaction parameters, such as temperature, time, and the use of solvents.

The process for preparing an adduct comprising a compound of formula (I) will now be described.

In one of its possible embodiments, the process comprises the following steps:
  a) preparing a solution of at least one compound of formula (I) in a solvent that may be: (i) protic or aprotic polar, selected from the group consisting of: alcohols, carbonylic solvents such as acetone, esters such as ethyl acetate, dimethylsulphoxide, acetonitrile, ethers, (ii) apolar, such as for example pentane, hexane, heptane, higher homologues and isomers thereof;
  b) preparing a suspension of the carbon allotrope in the polar or apolar solvent used for preparing the solution of the compound of formula (I);
  c) mixing the solution of the compound of formula (I) and the suspension of the carbon allotrope, by means of systems for mechanical or magnetic stirring, or by sonication with sonication equipment, for example by means of an ultrasonic bath;
  d) removing the solvent from the mixture obtained;
  e) optionally supplying thermal and/or mechanical energy and/or photon irradiation energy to the mixture obtained.

The procedure described in steps a)-c) results in obtaining a homogeneous dispersion of the nanofiller and of at least one pyrrole compound bearing a lipophilic substituent on the nitrogen atom and then obtaining a homogeneous dispersion of the pyrrole compound bearing a lipophilic substituent on the nitrogen atom, on the carbon filler. The solvents are removed before the next steps of energy transfer to the adduct between the carbon nanofiller and at least one pyrrole compound bearing a lipophilic substituent on the nitrogen atom.

The term solvent refers to the pyrrole compounds bearing a lipophilic substituent on the nitrogen atom and obviously not to the carbon allotrope, for which the solvent only acts as a dispersing medium. Preferably the solvent should be environmentally friendly.

In the rest of the present description the terms "carbon allotrope" and "carbon filler" are used interchangeably.

Generally, owing to the chemical nature of carbon, it is rather difficult to disperse the carbon fillers in liquid matrices. The use of ultrasound makes it possible to effect dispersion in reasonable times and improve the homogeneity of the dispersion of the carbon filler (even just a few seconds). Moreover, using sonication it is possible, to a varying degree, to separate the carbon nanofillers into the fundamental units. The carbon nanotubes can be separated into the individual tubes from the tangle in which they are intertwined with other tubes. It is advisable to use low-power sonicators, such as the classic ultrasonic baths. With suitable solvents it is also possible to perform at least partial exfoliation of a graphite having a varying starting number of stacked layers. Graphites with a small number of stacked layers have nanometric dimensions and are called nanographites. It is therefore preferred to contact the nanofiller with a liquid first, so as to obtain, by sonication and depending on the nanofiller, either so-called untangling of the carbon nanotubes, or exfoliation, more or less pronounced, of the graphite or nanographite. This procedure leads to improvement of contact between the nanofiller and the pyrrole compound bearing a lipophilic substituent on the nitrogen atom, and also results in increasing the exposed area of the nanofiller.

According to the present invention the term "sonochemistry" denotes the physicochemical discipline that studies the chemical reactions that occur in a solution irradiated with ultrasound. This irradiation gives rise, for a field intensity above a certain threshold value, to a phenomenon of cavitation in the solution. The gas microcavities (bubbles) present in the solution, on being subjected to successive expansion and contraction induced by the oscillating field of sound pressure, increase in size and then implode, producing regions with extremely high temperature and pressure. In these extreme conditions, chemical reactions may take place that are of considerable interest in the field of the synthesis of organic substances, polymerization processes, and degradation of toxic and harmful substances. By employing sonication techniques it is also possible to obtain amorphous materials which, without the extreme conditions typical of sonication, would have a natural tendency to crystallize.

The method of removing the solvent, according to step d), from the mixture obtained, may take place by any suitable method for removal of solvents, for example vacuum evaporation, spray drying, etc.

The mixture obtained after removing the solvent from the mixture containing the compound of formula (I) and the carbon allotrope may undergo a further step e), in which energy is transferred to the composition.

The addition reaction that leads to the formation of the adduct is carried out with energy transfer to the system consisting of the molecule containing the pyrrole ring bound to a diol, and the carbon allotrope. Energy transfer is performed in order to improve the interaction between the molecule containing the pyrrole ring bound to a diol and the carbon allotrope. In the absence of energy transfer, there is weaker interaction between the pyrrole ring bound to a diol and the carbon allotrope. A weaker interaction may lead to the partial release of the carbon allotrope from the molecule containing the pyrrole ring bound to a diol, especially if the adduct is in an environment of a polar nature.

The forms of energy that can be transferred to the composition to allow formation thereof are:
mechanical energy
thermal energy
photons Mechanical Energy The mixture that is obtained between the nanofiller and at least one pyrrole compound bearing a lipophilic substituent on the nitrogen atom, obtained by the process described above in steps a-c, is treated by a mechanical process.

The mechanical treatment consists of putting the powder obtained (nanofiller/SP) in a jar equipped with stainless-steel balls. Once closed, the jar is put in a planetary mixer and is rotated at a speed from 200 to 500 rpm/min for times from 1 to 360 minutes. The powder is discharged immediately thereafter.

The mechanical treatment referred to is used both for inducing disorder (exfoliation in the case of graphite) in order to obtain better distribution of SP on the nanofiller, and for inducing development of a much more stable interaction.

This is possible as it is known in chemistry that it is possible to induce chemical reactions of dry mixtures by subjecting them to mechanical forces. Mechanochemistry is a little-known branch of chemistry that is of considerable interest on account of its environmentally friendly character. A mechanochemical process can be initiated simply using pestle and mortar or using more unwieldy systems but with simple operation such as ball mills, used in the pharmaceutical industry and the food industry.

So-called planetary ball mills have cylindrical reactors, jars, held in a vertical position on a rotating platform. In mills with jars containing balls, use is made of the collisions between the balls, which typically number between 5 and 50. The efficiency with which a given mill operates in relation to a given mechanochemical transformation is closely linked to the frequency of the collisions between the balls and the inside wall of the jar and to the mechanical energy transferred. These quantities depend in their turn on the dynamics of the balls, their size and how many there are, on the frequency of oscillation, or work, of the mill, and on the total amount of powder in the reactor.

Thermal Energy

The mixture that is obtained between the nanofiller and at least one pyrrole compound bearing a lipophilic substituent on the nitrogen atom, obtained by the process described above in steps a-c, is treated by a thermal process.

The thermal treatment consists of putting the powder obtained (nanofiller/SP) in a reaction flask equipped with a condenser or in a sealed ampoule. Once the reactor has been set up on a hot plate, the reaction is carried out at temperatures from 130° C. to 180° C. Heating is maintained from a minimum of 2 hours to 12. The thermal treatment induces the formation of stable interactions.

Photons

The mixture that is obtained between the nanofiller and at least one pyrrole compound bearing a lipophilic substituent on the nitrogen atom, obtained by the process described above in steps a-c, is treated by an irradiation process using a lamp of a suitable wavelength.

The treatment with photons consists of putting the powder obtained (nanofiller/SP) in a laboratory crystallizer forming a thin layer or putting the powder in a sealed quartz ampoule. Once the reactor is set up inside a dark chamber equipped with a low-pressure mercury lamp at 254 nm (or using a Rayonet® reactor equipped with the same type of lamp) the mixture is irradiated for times varying from 30 to 180 minutes. After this time the mixture is discharged and analysed.

With an adduct according to the present invention it is possible to obtain stable suspensions of carbon nanofillers both in aqueous media and in other substrates such as polymer blends or rubber, so as to obtain homogeneous products that have the particular characteristics of the carbon nanofillers, for example high mechanical properties, high electrical conductivity, resistance to high temperatures, flame-retardant properties.

With an adduct according to the present invention it is also possible to obtain uniform, continuous layers of carbon black fillers on various substrates in order to obtain highly conductive surfaces.

Some examples of preparation of the adduct comprising a pyrrole compound bearing a lipophilic substituent on the nitrogen atom and a carbon allotrope according to the present invention will be described below.

The adduct according to the present invention will be better illustrated by the examples presented hereunder that illustrate the steps of the process of preparation from said adduct.

BRIEF DESCRIPTION OF THE DRAWINGS

Features and advantages of the invention will be better understood from the description of preferred embodiments, illustrated for example in the appended drawings; in which:

FIG. 1 shows the chromatogram and the mass spectrum obtained after GC-MS analysis of 1-hexyl-2,5-dimethyl-1H-pyrrole;

FIG. 2 shows the $^1$H NMR spectrum at 400 MHz in CDCl$_3$ of 1-hexyl-2,5-dimethyl-1H-pyrrole;

FIG. 3 shows the FTIR spectrum of the adduct of 1-hexyl-2,5-dimethyl-1H-pyrrole with CB N 326;

FIG. 4 shows the chromatogram and the mass spectrum obtained after GC-MS analysis of 1,6-bis(2,5-dimethyl-1H-pyrrol-1-yl)hexane;

FIG. 5 shows the FTIR spectrum of the adduct of 1,6-bis (2,5-dimethyl-1H-pyrrol-1-yl)hexane with nanographite;

FIG. 6 shows the $^1$H NMR spectrum at 400 MHz in CDCl$_3$ of 2,5-dimethyl-1-(3-(trimethoxysilyl)propyl)-1H-pyrrole;

FIG. 7 shows the FTIR spectrum of the adduct of 2,5-dimethyl-1-(3-(trimethoxysilyl)propyl)-1H-pyrrole with nanographite;

FIG. 8 shows the $^1$H NMR spectrum at 400 MHz in CDCl$_3$ of 3-(2,5-dimethyl-1H-pyrrol-1-yl)-N,N-dimethyl-propan-1-amine;

FIG. 9 shows the $^1$H NMR spectrum at 400 MHz in CDCl$_3$ of O-(2-(2,5-dimethylpyrrol-1-yl)propyl)-O'-(2-methoxyethyl)polypropylene glycol.

EXAMPLES

All the chemicals used in the syntheses given in the following examples were obtained from Aldrich and were used without further purification.

The compositions obtained in the examples presented below were analysed as follows:
- analysis by infrared spectroscopy (FT-IR using KBr pellet): adduct/KBr weight ratios of 1:500 were used, and about 80 mg of mixture for forming the pellet. The pellet was analysed using a Fourier transform IR spectrophotometer (Varian 640-IR FT-IR spectrometer with ATR option). The samples were irradiated in a range between 2.5 and 20 µm (or between 4000 and 500 cm$^{-1}$)
- UV spectroscopy: the suspensions of adduct (3 mL) were placed, using a Pasteur pipette, in quartz cuvettes with a 1 cm optical path (volume 1 or 3 mL) and were analysed using a UV-Vis spectrophotometer. The instrument is zeroed with the pure solvent and a UV spectrum is recorded from 200 to 340 nm. A blank of the solvent used was recorded. The UV-visible spectrum gave the intensity of absorption as a function of the wavelength of the radiation between 200 and 750 nm.
- stability in the solvent: after treatment, the powder was placed in a laboratory vial, the appropriate solvent was added (concentration of 1 mg/mL) and it was sonicated for 10 minutes. At the end of sonication (at time t=0) it was analysed by UV spectroscopy. This analysis was then repeated after 1 day and 1 week.

Example 1—Synthesis of
1-hexyl-2,5-dimethyl-1H-pyrrole (Hexyl Pyrrole, HP)

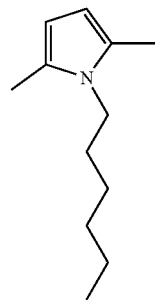

Empirical formula: C12H21N
Molar mass: 179.30

A 100-mL single-neck flask equipped with a magnetic stirrer is charged with 3.75 g (0.151 mol) of hexylamine and 4.25 g (0.151 mol) of 2,5-hexanedione. The mixture is stirred for 5 hours at 150° C.

The product is isolated as a light yellow oil, with a yield of 95% and is analysed by gas chromatography coupled to mass spectrometry (GC-MS) and nuclear magnetic resonance (NMR). FIG. 1 shows the chromatogram coupled to the mass spectrum. The mass determined in this experiment corresponds to the theoretical mass of the compound 1-hexyl-2,5-dimethyl-1H-pyrrole. FIG. 2 shows the $^1$H-NMR spectrum.

Example 2—Synthesis of
1-hexyl-2,5-dimethyl-1H-pyrrole with Reactants
Supported on Graphite as the Carbon Allotrope The graphite used is Synthetic Graphite 8427, acquired from Asbury Graphite Mills Inc., with a minimum carbon content of 99.8 wt % and a surface area of 330 m$^2$/g.

A 100-mL single-neck flask equipped with a magnetic stirrer is charged with 3.75 g (0.151 mol) of hexylamine, 4.25 g (0.151 mol) of 2,5-hexanedione and 10 g of graphite. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform ($CDCl_3$) is added at room temperature. The test tube is agitated manually for 2 minutes, at room temperature. The suspension contained in the test tube is left to decant. This liquid is analysed by $^1$H-NMR spectroscopy, which revealed the same peaks as shown in FIG. 2 and thus confirmed the expected structure for the compound 1-hexyl-2,5-dimethyl-1H-pyrrole.

Example 3—Synthesis of
1-hexyl-2,5-dimethyl-1H-pyrrole with Reactants Supported on Carbon Black as the Carbon Allotrope The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.

A 100-mL single-neck flask equipped with a magnetic stirrer is charged with 3.75 g (0.151 mol) of hexylamine, 4.25 g (0.151 mol) of 2,5-hexanedione and 10 g of carbon black. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform ($CDCl_3$) is added at room temperature. The test tube is agitated manually for 2 minutes, at room temperature. The suspension contained in the test tube is left to decant. This liquid is analysed by $^1$H-NMR spectroscopy, which revealed the same peaks as shown in FIG. 2 and thus confirmed the expected structure for the compound 1-hexyl-2,5-dimethyl-1H-pyrrole.

Example 4—Adduct of
1-hexyl-2,5-dimethyl-1H-pyrrole with Carbon Black

The hexylpyrrole used is that synthesized in example 1.
The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.

A 250-mL single-neck flask is charged with 10 g of carbon black and 100 mL of acetone. The suspension is sonicated in an ultrasonic bath for 15 minutes. After this time, a solution of 2.33 g of hexylpyrrole in 20 mL of acetone is added. The resultant suspension is sonicated for a further 15 minutes. The solvent is removed at reduced pressure. A powder is obtained, consisting of carbon black with adsorbed hexylpyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed repeatedly with distilled water. The filtrate was colourless. The wash water is analysed by UV spectroscopy.

The samples of adduct that were collected after the indicated thermal treatment times and washing as illustrated, are characterized by FT-IR analysis, performed by preparing a pellet of the sample of adduct in KBr. The IR spectrum in FIG. 3 shows peaks that are typical of sequences of groups ($CH_2$), at 2900 $cm^{-1}$ and 2830 $cm^{-1}$—peaks that are not present in the IR spectrum of the starting allotrope.

Example 5—Adduct of
1-hexyl-2,5-dimethyl-1H-pyrrole with Graphite

The hexylpyrrole used is that synthesized in example 1.
The graphite used is Synthetic Graphite 8427, acquired from Asbury Graphite Mills Inc., with a minimum carbon content of 99.8 wt % and a surface area of 330 $m^2/g$.

A 250-mL single-neck flask is charged with 10 g of graphite and 100 mL of acetone. The suspension is sonicated in an ultrasonic bath for 15 minutes. After this time, a solution of 2.33 g of hexylpyrrole in 20 mL of acetone is added. The resultant suspension is sonicated for a further 15 minutes. The solvent is removed at reduced pressure. A powder is obtained, consisting of graphite with adsorbed hexylpyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed repeatedly with distilled water. The filtrate was colourless. The wash water is analysed by UV spectroscopy.

The samples of adduct, collected after the indicated thermal treatment times and washing as illustrated, are characterized by FT-IR analysis, performed by preparing a pellet of the sample of adduct in KBr.

Example 6—Synthesis of
1,6-bis(2,5-dimethyl-1H-pyrrol-1-yl)hexane
(Hexamethylene Bispyrrole, HBP)

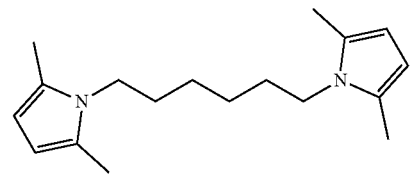 [SMILES: Cc1ccc(C)n1CCCCCCn1c(C)ccc1C]

Empirical formula: $C_{18}H_{28}N_2$
Molar mass: 272.43

A 100-mL single-neck flask equipped with a magnetic stirrer is charged with 1 g (8.6 mmol) of hexamethylenediamine and 1.96 g (17.2 mmol) of 2,5-hexanedione. The mixture is stirred for 4 hours at 150° C.

The product is isolated as dark yellow oil, with a yield of 80% and is analysed by gas chromatography coupled to mass spectrometry (GC-MS) and nuclear magnetic resonance (NMR). FIG. 4 shows the chromatogram coupled to the mass spectrum. The mass determined by this experiment corresponds to the theoretical mass of the compound 1,6-bis(2,5-dimethyl-1H-pyrrol-1-yl)hexane.

Example 7—Synthesis of
1,6-bis(2,5-dimethyl-1H-pyrrol-1-yl)hexane with Reactants Supported on Graphite as the Carbon Allotrope The graphite used is Synthetic Graphite 8427, acquired from Asbury Graphite Mills Inc., with a minimum carbon content of 99.8 wt % and a surface area of 330 $m^2/g$.

A 100-mL single-neck flask equipped with a magnetic stirrer is charged with 1 g (8.6 mmol) of hexamethylenediamine, 1.96 g (17.2 mmol) of 2,5-hexanedione and 3 g of graphite. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform ($CDCl_3$) is added at room temperature. The test tube is agitated manually for 2 minutes, at room temperature. The suspension contained in the test tube is left to decant. This liquid is analysed by $^1$H-NMR spectroscopy.

Example 8—Synthesis of 1,6-bis(2,5-dimethyl-1H-pyrrol-1-yl)hexane with Reactants Supported on Carbon Black as the Carbon Allotrope The carbon black used is Carbon Black N326 (CB) (Cabot), having the following characteristics: 30 nm average diameter of the spherical particles, surface area equal to 77 $m^2$/g (determined by nitrogen absorption), absorption of DBP equal to 85 mL/100 g.

A 100-mL single-neck flask equipped with a magnetic stirrer is charged with 1 g (8.6 mmol) of hexamethylenediamine, 1.96 g (17.2 mmol) of 2,5-hexanedione and 3 g of carbon black. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform ($CDCl_3$) is added at room temperature. The test tube is agitated manually for 2 minutes, at room temperature. The suspension contained in the test tube is left to decant. This liquid is analysed by $^1$H-NMR spectroscopy.

Example 9—Adduct of 1,6-bis(2,5-dimethyl-1H-pyrrol-1-yl)hexane with Nanographite The pyrrole compound used (hexamethylene bispyrrole) is that synthesized in example 6.

The graphite used is Synthetic Graphite 8427, acquired from Asbury Graphite Mills Inc., with a minimum carbon content of 99.8 wt % and a surface area of 330 $m^2$/g.

A 250-mL single-neck flask is charged with 10 g of graphite and 100 mL of acetone. The suspension is sonicated in an ultrasonic bath for 15 minutes. After this time, a solution of 2 g of hexamethylene bispyrrole in 20 mL of acetone is added. The resultant suspension is sonicated for a further 15 minutes. The solvent is removed at reduced pressure. A powder is obtained, consisting of graphite with adsorbed hexamethylene bispyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed repeatedly with distilled water. The filtrate was colourless. The wash water is analysed by UV spectroscopy.

The samples of adduct that were collected after the indicated thermal treatment times and washing as illustrated, are characterized by FT-IR analysis, performed by preparing a pellet of the sample of adduct in KBr. The IR spectrum in FIG. 5 shows peaks that are typical of sequences of groups ($CH_2$), at 2910 $cm^{-1}$ and 2840 $cm^{-1}$—peaks that are not present in the IR spectrum of the starting allotrope.

Example 10—Adduct of 1,6-bis(2,5-dimethyl-1H-pyrrol-1-yl)hexane with Carbon Black The pyrrole compound used (hexamethylene bispyrrole) is that synthesized in example 6.

The carbon black used is Carbon Black N326 (CB) (Cabot), having the following characteristics: 30 nm average diameter of the spherical particles, surface area equal to 77 $m^2$/g (determined by nitrogen absorption), absorption of DBP equal to 85 mL/100 g.

A 250-mL single-neck flask is charged with 10 g of carbon black and 100 mL of acetone. The suspension is sonicated in an ultrasonic bath for 15 minutes. After this time, a solution of 2 g of hexamethylene bispyrrole in 20 mL of acetone is added. The resultant suspension is sonicated for a further 15 minutes. The solvent is removed at reduced pressure. A powder is obtained, consisting of carbon black with adsorbed hexamethylene bispyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed repeatedly with distilled water. The filtrate was colourless. The wash water is analysed by UV spectroscopy.

The samples of adduct that were collected after the indicated thermal treatment times and washing as illustrated, are characterized by FT-IR analysis, performed by preparing a pellet of the sample of adduct in KBr.

Example 11—Synthesis of 2,5-dimethyl-1-(3-(trimethoxysilyl)propyl)-1H-pyrrole (Pyrrolopropyl Trimethoxysilane (PPTMS)

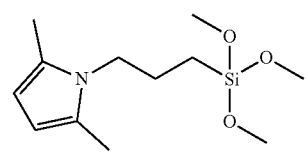 [SMILES: CO[Si](CCCn1c(C)ccc1C)(OC)OC]

Empirical formula: $C_{12}H_{23}NO_3Si$
Molar mass: 257.14

A 100-mL single-neck flask equipped with a magnetic stirrer is charged with 1 g (5.58 mmol) of 3-(trimethoxysilyl)propan-1-amine and 0.640 g (5.58 mmol) of 2,5-hexanedione. The mixture is stirred for 6 hours at 150° C. The product is isolated as a sticky solid of an intense light yellow colour and is analysed by gas chromatography coupled to mass spectrometry (GC-MS) and nuclear magnetic resonance (NMR). The GC-MS analysis shows the compound 2,5-dimethyl-1-(3-(trimethoxysilyl)propyl)-1H-pyrrole as well as unreacted 3-(trimethoxysilyl)propan-1-amine. The yellow solid was then dissolved in dichloromethane. The solution obtained was washed with deionized water. The organic phase was dried over $Na_2SO_4$ and thoroughly dried at reduced pressure. The solid isolated is the pure compound 2,5-dimethyl-1-(3-(trimethoxysilyl)propyl)-1H-pyrrole. The weight of this compound allowed us to calculate a yield equal to 89%.

FIG. 6 shows the $^1$H-NMR spectrum.

Example 12—Synthesis of 2,5-dimethyl-1-(3-(trimethoxysilyl)propyl)-1H-pyrrole with Reactants Supported on Graphite as the Carbon Allotrope The graphite used is Synthetic Graphite 8427, acquired from Asbury Graphite Mills Inc., with a minimum carbon content of 99.8 wt % and a surface area of 330 m$^2$/g.

A 100-mL single-neck flask equipped with a magnetic stirrer is charged with 1 g (5.58 mmol) of 3-(trimethoxysilyl)propan-1-amine, 0.640 g (5.58 mmol) of 2,5-hexanedione and 3 g of graphite. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform (CDCl$_3$) is added at room temperature. The test tube is agitated manually for 2 minutes, at room temperature. The suspension contained in the test tube is left to decant. This liquid is analysed by $^1$H-NMR spectroscopy, which revealed the same peaks as shown in FIG. 6 and thus confirmed the expected structure for the compound 2,5-dimethyl-1-(3-(trimethoxysilyl)propyl)-1H-pyrrole.

Example 13—Synthesis of 2,5-dimethyl-1-(3-(trimethoxysilyl)propyl)-1H-pyrrole with Reactants Supported on Carbon Black as the Carbon Allotrope The carbon black used is Carbon Black N326 (CB) (Cabot), having the following characteristics: 30 nm average diameter of the spherical particles, surface area equal to 77 m$^2$/g (determined by nitrogen absorption), absorption of DBP equal to 85 mL/100 g.

A 100-mL single-neck flask equipped with a magnetic stirrer is charged with 1 g (5.58 mmol) of 3-(trimethoxysilyl)propan-1-amine, 0.640 g (5.58 mmol) of 2,5-hexanedione and 3 g of carbon black. The flask is equipped with a magnetic stirrer and the mixture is subjected to slow rotation, at a temperature of 150° C. for 2 hours. The reaction mixture is then brought to room temperature. A sample of solid is taken and is put in a test tube. Deuterated chloroform (CDCl$_3$) is added at room temperature. The test tube is agitated manually for 2 minutes, at room temperature. The suspension contained in the test tube is left to decant. This liquid is analysed by $^1$H-NMR spectroscopy, which revealed the same peaks as shown in FIG. 6 and thus confirmed the expected structure for the compound 2,5-dimethyl-1-(3-(trim ethoxysilyl)propyl)-1H-pyrrole.

Example 14—Adduct of 2,5-dimethyl-1-(3-(trimethoxysilyl)propyl)-1H-pyrrole with Graphite The pyrrole compound used is that synthesized in example 11.

The graphite used is Synthetic Graphite 8427, acquired from Asbury Graphite Mills Inc., with a minimum carbon content of 99.8 wt % and a surface area of 330 m$^2$/g.

A 250-mL single-neck flask is charged with 10 g of graphite and 100 mL of acetone. The suspension is sonicated in an ultrasonic bath for 15 minutes. After this time, a solution of 2 g of hexamethylene bispyrrole in 20 mL of acetone is added. The resultant suspension is sonicated for a further 15 minutes. The solvent is removed at reduced pressure. A powder is obtained, consisting of graphite with adsorbed 2,5-dimethyl-1-(3-(trimethoxysilyl)propyl)-1H-pyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed 3 times with deionized water. The filtrate was colourless. The water from the fourth washing is analysed by UV spectroscopy: no absorption is detected.

The samples of adduct that were collected after the indicated thermal treatment times and washing as illustrated, are characterized by FT-IR analysis, performed by preparing a pellet of the sample of adduct in KBr. The IR spectrum in FIG. 7 shows peaks that are typical of sequences of groups (CH$_2$), at 2910 cm$^{-1}$ and 2827 cm$^{-1}$—peaks that are not present in the IR spectrum of the starting allotrope.

Example 15—Adduct of 2,5-dimethyl-1-(3-(trimethoxysilyl)propyl)-1H-pyrrole with Carbon Black The pyrrole compound used is that synthesized in example 11.

The carbon black used is Carbon Black N326 (CB) (Cabot), having the following characteristics: 30 nm average diameter of the spherical particles, surface area equal to 77 m$^2$/g (determined by nitrogen absorption), absorption of DBP equal to 85 mL/100 g.

A 250-mL single-neck flask is charged with 10 g of carbon black and 100 mL of acetone. The suspension is sonicated in an ultrasonic bath for 15 minutes. After this time, a solution of 2 g of hexamethylene bispyrrole in 20 mL of acetone is added. The resultant suspension is sonicated for a further 15 minutes. The solvent is removed at reduced pressure. A powder is obtained, consisting of carbon black with adsorbed 2,5-dimethyl-1-(3-(trimethoxysilyl)propyl)-1H-pyrrole.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed 3 times with deionized water. The filtrate was colourless. The water from the fourth washing is analysed by UV spectroscopy: no absorption is detected.

Example 16—Synthesis of 3-(2,5-dimethyl-1H-pyrrol-1-yl)-N,N-dimethylpropan-1-amine (Dimethylamine Propane Pyrrole DAPP)

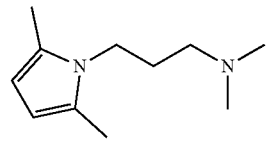

Empirical formula: C$_{11}$H$_{20}$N$_2$

Molar mass: 180.16

A 100-mL single-neck flask equipped with a magnetic stirrer is charged with 1 g (9.7 mmol) of N$^1$,N$^1$-dimethylpropane-1,3-diamine and 1.10 g (9.7 mmol) of 2,5-hexanedione. The mixture is stirred for 6 hours at 150° C. The product is isolated as an amber-coloured oil and is analysed by nuclear magnetic resonance (NMR), which shows only the expected compound 3-(2,5-dimethyl-1H-pyrrol-1-yl)-N, N-dimethylpropan-1-amine. The weight found and the chemical purity observed by NMR analysis allowed evaluation of a yield equal to 95%. FIG. 8 shows the ¹H-NMR spectrum.

Example 17—Synthesis of 3-(2,5-dimethyl-1H-pyrrol-1-yl)-N,N-dimethylpropan-1-amine with Reactants Supported on Graphite as the Carbon Allotrope The graphite used is Synthetic Graphite 8427, acquired from Asbury Graphite Mills Inc., with a minimum carbon content of 99.8 wt % and a surface area of 330 m²/g.

A 100-mL single-neck flask equipped with a magnetic stirrer is charged with 1 g (9.7 mmol) of $N^1,N^1$-dimethylpropane-1,3-diamine, 1.10 g (9.7 mmol) of 2,5-hexanedione and 3 g of graphite. The flask is equipped with a magnetic stirrer and the mixture is subjected to slow rotation, at a temperature of 150° C. for 2 hours. The reaction mixture is then brought to room temperature. A sample of solid is taken and is put in a test tube. Ethyl acetate is added at room temperature. The test tube is agitated manually for 2 minutes, at room temperature. The suspension contained in the test tube is left to decant. The supernatant is analysed by thin-layer chromatography, performed with ethyl acetate/hexane solvent mixture (1/9). UV analysis shows haloes with the same $R_f$ (0.6) for the substance 3-(2,5-dimethyl-1H-pyrrol-1-yl)-N,N-dimethylpropan-1-amine obtained in example 16 and for the substance extracted with ethyl acetate from the graphite, as just described.

Example 18—Synthesis of 3-(2,5-dimethyl-1H-pyrrol-1-yl)-N,N-dimethylpropan-1-amine with Reactants Supported on Carbon Black as the Carbon Allotrope The carbon black used is Carbon Black N326 (CB) (Cabot), having the following characteristics: 30 nm average diameter of the spherical particles, surface area equal to 77 m²/g (determined by nitrogen absorption), absorption of DBP equal to 85 mL/100 g.

A 100-mL single-neck flask equipped with a magnetic stirrer is charged with 1 g (9.7 mmol) of $N^1,N^1$-dimethylpropane-1,3-diamine, 1.10 g (9.7 mmol) of 2,5-hexanedione and 3 g of carbon black. The flask is equipped with a magnetic stirrer and the mixture is subjected to slow rotation, at a temperature of 150° C. for 2 hours. The reaction mixture is then brought to room temperature. A sample of solid is taken and is put in a test tube. Ethyl acetate is added at room temperature. The test tube is agitated manually for 2 minutes, at room temperature. The suspension contained in the test tube is left to decant. The supernatant is analysed by thin-layer chromatography, performed with ethyl acetate/hexane solvent mixture (1/9). UV analysis shows haloes with the same $R_f$ (0.6) for the substance 3-(2,5-dimethyl-1H-pyrrol-1-yl)-N,N-dimethylpropan-1-amine obtained in example 16 and for the substance extracted with ethyl acetate from the graphite, as just described.

Example 19—Adduct of 3-(2,5-dimethyl-1H-pyrrol-1-yl)-N,N-dimethylpropan-1-amine (DAPP) with Graphite The pyrrole compound used is that synthesized in example 16.

The graphite used is Synthetic Graphite 8427, acquired from Asbury Graphite Mills Inc., with a minimum carbon content of 99.8 wt % and a surface area of 330 m²/g.

A 250-mL single-neck flask is charged with 10 g of graphite and 100 mL of acetone. The suspension is sonicated in an ultrasonic bath for 15 minutes. After this time, a solution of 2 g of DAPP in 20 mL of acetone is added. The resultant suspension is sonicated for a further 15 minutes. The solvent is removed at reduced pressure. A powder is obtained, consisting of graphite with absorbed DAPP.

0.300 g of powder is put in a 30-mL ampoule equipped with a magnetic stirrer. The reaction mixture is heated at a temperature of 180° C. for 2 hours.

After this time the powder is cooled to 25° C. The powder was put in a Büchner with septum and was washed 3 times with deionized water. The filtrate was colourless. The water from the fourth washing is analysed by UV spectroscopy: no absorption is detected.

Example 20—Synthesis of O-(2-(2,5-dimethylpyrrol-1-yl)propyl)-O'-(2-methoxyethyl)polypropylene Glycol (pyrroloPEG, PPEG)

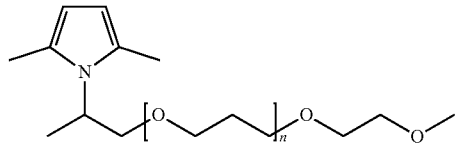

A 100-mL single-neck flask equipped with a magnetic stirrer is charged with 1 g (1.6 mmol) of O-(2-aminopropyl)-O'-(2-methoxyethyl)polypropylene glycol (Mn=600) and 0.190 g (1.6 mmol) of 2,5-hexanedione. The mixture is stirred for 6 hours at 150° C. The product is isolated as a very viscous amber-coloured liquid and is analysed by nuclear magnetic resonance (NMR), which shows only the expected compound O-(2-(2,5-dimethylpyrrol-1-yl)propyl)-O'-(2-methoxyethyl)polypropylene glycol. The weight found and the chemical purity observed by NMR analysis allowed evaluation of a yield equal to 97%. FIG. 9 shows the ¹H-NMR spectrum.

Example 21—Synthesis of O-(2-(2,5-dimethylpyrrol-1-yl)propyl)-O'-(2-methoxyethyl)polypropylene Glycol with Reactants Supported on Graphite as the Carbon Allotrope The graphite used is Synthetic Graphite 8427, acquired from Asbury Graphite Mills Inc., with a minimum carbon content of 99.8 wt % and a surface area of 330 m²/g.

A 100-mL single-neck flask equipped with a magnetic stirrer is charged with 1 g (1.6 mmol) of O-(2-aminopropyl)-O'-(2-methoxyethyl)polypropylene glycol, 0.190 g (1.6 mmol) of 2,5-hexanedione and 3 g of graphite.

Example 22—Adduct of O-(2-(2,5-dimethylpyrrol-1-yl)propyl)-O'-(2-methoxyethyl)polypropylene Glycol with Graphite as the Carbon Allotrope The pyrrole compound used is that synthesized in example 19.

The graphite used is Synthetic Graphite 8427, acquired from Asbury Graphite Mills Inc., with a minimum carbon content of 99.8 wt % and a surface area of 330 m²/g.

A 250-mL single-neck flask is charged with 10 g of graphite and 100 mL of acetone. The suspension is sonicated in an ultrasonic bath for 15 minutes. After this time, a solution of 2 g of O-(2-(2,5-dimethylpyrrol-1-yl)propyl)-O'-(2-methoxyethyl)polypropylene glycol in 20 mL of acetone is added. The resultant suspension is sonicated for a further 15 minutes. The solvent is removed at reduced pressure. A powder is obtained, consisting of graphite with adsorbed O-(2-(2,5-dimethylpyrrol-1-yl)propyl)-O'-(2-methoxyethyl)polypropylene glycol.

0.300 g of powder is put in a 30-mL ampoule equipped with a magnetic stirrer. The reaction mixture is heated at a temperature of 180° C. for 2 hours.

After this time the powder is cooled to 25° C.

Examples 23-26—Stability Tests of Dispersions of the Adducts of Pyrrole Compounds with Graphite in Ethyl Acetate The graphite is Synthetic Graphite 8427, acquired from Asbury Graphite Mills Inc., with a minimum carbon content of 99.8 wt % and a surface area of 330 $m^2/g$.

The purpose of this test is to verify the capacity of the adduct, consisting of the carbon allotrope, graphite and the pyrrole compound, to form suspensions that are stable over time. The stability in solvents was evaluated in an organic molecule such as ethyl acetate.

Procedure:

10 mg of powdered adduct was put in a 10-mL flask and ethyl acetate (10 mL) was added. The mixture was sonicated in a 2-litre ultrasonic bath, with a power of 260 W, for 20 minutes.

The suspensions of adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

The results of the stability tests are given in Table 1.

TABLE 1

Stability tests of dispersions in ethyl acetate of the adducts of pyrrole compounds with graphite[a]

| | Example | | | |
|---|---|---|---|---|
| | 23 | 24 | 25 | 26 |
| Adduct from Example No. | 5 | 9 | 14 | 22 |
| Pyrrole compound | HP[b] | HBP[c] | PPTMS[d] | PPEG[e] |
| Absorbance at 300 nm | | | | |
| t = 0 | 2.03 | 4.09 | 4.09 | 4.09 |
| t = 1 week | 1.10 | 4.09 | 4.09 | 4.09 |

[a]The graphite is Synthetic Graphite 8427, acquired from Asbury Graphite Mills Inc., with a minimum carbon content of 99.8 wt % and a surface area of 330 $m^2/g$.
[b]HP = 1-hexyl-2,5-dimethyl-1H-pyrrole (hexyl pyrrole)
[c]HBP = 1,6-bis(2,5-dimethyl-1H-pyrrol-1-yl)hexane (hexamethylene bispyrrole)
[d]PPTMS = 2,5-dimethyl-1-(3-(trimethoxysilyl)propyl)-1H-pyrrole (pyrrolopropyl trimethoxysilane)
[e]PPEG = O-(2-(2,5-dimethylpyrrol-1-yl)propyl)-O'-(2-methoxyethyl)polypropylene glycol (pyrroloPEG)

Examples 27-29—Stability Tests of Dispersions in Ethyl Acetate of the Adducts of Pyrrole Compounds with Carbon Black The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.

The purpose of this test is to verify the capacity of the adduct, consisting of the carbon allotrope, carbon black, and the pyrrole compound, to form suspensions that are stable over time. The stability in solvents was evaluated in an organic molecule such as ethyl acetate.

Procedure:

10 mg of the powdered adduct was put in a 10-mL flask and ethyl acetate (10 mL) was added. The mixture was sonicated in a 2-litre ultrasonic bath, with a power of 260 W, for 20 minutes.

The suspensions of the adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

The results of the stability tests are given in Table 2.

TABLE 2

Stability tests of dispersions in ethyl acetate of the adducts of pyrrole compounds with carbon black[a]

| | Example | | |
|---|---|---|---|
| | 27 | 28 | 29 |
| Adduct from Example No. | 4 | 10 | 15 |
| Pyrrole compound | HP[b] | HBP[c] | PPTMS[d] |
| Absorbance at 300 nm | | | |
| t = 0 | 2.90 | 4.09 | 3.23 |
| t = 1 week | 1.21 | 4.09 | 2 |

[a]The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.
[b]HP = 1-hexyl-2,5-dimethyl-1H-pyrrole (hexyl pyrrole)
[c]HBP = 1,6-bis(2,5-dimethyl-1H-pyrrol-1-yl)hexane (hexamethylene bispyrrole)
[d]PPTMS = 2,5-dimethyl-1-(3-(trimethoxysilyl)propyl)-1H-pyrrole (pyrrolopropyl trimethoxysilane)

Examples 30-34—Stability Tests of Dispersions in n-Hexane of the Adducts of Pyrrole Compounds with Graphite The graphite is Synthetic Graphite 8427, acquired from Asbury Graphite Mills Inc., with a minimum carbon content of 99.8 wt % and a surface area of 330 $m^2/g$.

The purpose of this test is to verify the capacity of the adduct, consisting of the carbon allotrope, graphite, and the pyrrole compound, to form suspensions that are stable over time. The stability in solvents was evaluated in an apolar medium, n-hexane.

Procedure:

10 mg of the powdered adduct was put in a 10-mL flask, and n-hexane (10 mL) was added. The mixture was sonicated in a 2-litre ultrasonic bath, with a power of 260 W, for 20 minutes.

The suspensions of the adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

The results of the stability tests are given in Table 3.

TABLE 3

Stability tests of dispersions in n-hexane of the adducts of pyrrole compounds with graphite[a]

|  | Example | | | | |
| --- | --- | --- | --- | --- | --- |
|  | 30 | 31 | 32 | 33 | 34 |
| Adduct from Example No. | 5 | 9 | 14 | 19 | 22 |
| Pyrrole compound | HP[b] | HBP[c] | PPTMS[d] | DAPP[e] | PPEG[e] |
| Absorbance at 300 nm | | | | | |
| t = 0 | 4.10 | 4.09 | 3.20 | 2 | 4.03 |
| t = 1 day | 4.10 | 4.08 | 3.01 | 1.9 | 4.03 |

[a]The graphite is Synthetic Graphite 8427, acquired from Asbury Graphite Mills Inc., with a minimum carbon content of 99.8 wt % and a surface area of 330 $m^2/g$.
[b]HP = 1-hexyl-2,5-dimethyl-1H-pyrrole (hexyl pyrrole)
[c]HBP = 1,6-bis(2,5-dimethyl-1H-pyrrol-1-yl)hexane (hexamethylene bispyrrole)
[d]PPTMS = 2,5-dimethyl-1-(3-(trimethoxysilyl)propyl)-1H-pyrrole (pyrrolopropyl trimethoxysilane)
[e]DAPP = 3-(2,5-dimethyl-1H-pyrrol-1-yl)-N,N-dimethylpropan-1-amine (dimethylamine propane pyrrole)
[e]PPEG = O-(2-(2,5-dimethylpyrrol-1-yl)propyl)-O'-(2-methoxyethyl)polypropylene glycol (pyrroloPEG)

Examples 35-37—Stability Tests of Dispersions in n-Hexane of the Adducts of Pyrrole Compounds with Carbon Black The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.

The purpose of this test is to verify the capacity of the adduct, consisting of the carbon allotrope, carbon black, and the pyrrole compound, to form suspensions that are stable over time. The stability in solvents was evaluated in an apolar medium, n-hexane.

Procedure:

10 mg of the powdered adduct was put in a 10-mL flask, and n-hexane (10 mL) was added. The mixture was sonicated in a 2-litre ultrasonic bath, with a power of 260 W, for 20 minutes.

The suspensions of adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

The results of the stability tests are given in Table 4.

TABLE 4

Stability tests of dispersions in n-hexane of the adducts of pyrrole compounds with carbon black[a]

|  | Example | | |
| --- | --- | --- | --- |
|  | 35 | 36 | 37 |
| Adduct from Example No. | 4 | 10 | 15 |
| Pyrrole compound | HP[b] | HBP[c] | PPTMS[d] |
| Absorbance at 300 nm | | | |
| t = 0 | 4.08 | 4.0 | 4.02 |
| t = 1 day | 4.09 | 4.0 | 4.01 |

[a]The carbon black used is Carbon Black N326 (CB) (Cabot), having the following characteristics: 30 nm average diameter of the spherical particles, surface area equal to 77 $m^2/g$ (determined by nitrogen absorption), absorption of DBP equal to 85 mL/100 g.
[b]HP = 1-hexyl-2,5-dimethyl-1H-pyrrole (hexyl pyrrole)
[c]HBP = 1,6-bis(2,5-dimethyl-1H-pyrrol-1-yl)hexane (hexamethylene bispyrrole)
[d]PPTMS = 2,5-dimethyl-1-(3-(trimethoxysilyl)propyl)-1H-pyrrole (pyrrolopropyl trimethoxysilane)

Examples 38-40—Stability Tests of Dispersions in Toluene of the Adducts of Pyrrole Compounds with Graphite The graphite is Synthetic Graphite 8427, acquired from Asbury Graphite Mills Inc., with a minimum carbon content of 99.8 wt % and a surface area of 330 $m^2/g$.

The purpose of this test is to verify the capacity of the adduct, consisting of the carbon allotrope, graphite, and the pyrrole compound, to form suspensions that are stable over time. The stability in solvents was evaluated in an organic solvent such as toluene.

Procedure:

10 mg of the powdered adduct was put in a 10-mL flask and toluene (10 mL) was added. The mixture was sonicated in a 2-litre ultrasonic bath, with a power of 260 W, for 20 minutes.

The suspensions of adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

The results of the stability tests are given in Table 5.

TABLE 5

Stability tests of dispersions in toluene of the adducts of pyrrole compounds with graphite[a]

|  | Example | | |
| --- | --- | --- | --- |
|  | 38 | 39 | 40 |
| Adduct from Example No. | 5 | 9 | 14 |
| Pyrrole compound | HP[b] | HBP[c] | PPTMS[d] |
| Absorbance at 300 nm | | | |
| t = 0 | 4.09 | 4.09 | 3.32 |
| t = 1 week | 4.09 | 4.09 | 3.00 |

[a]The graphite is Synthetic Graphite 8427, acquired from Asbury Graphite Mills Inc., with a minimum carbon content of 99.8 wt % and a surface area of 330 $m^2/g$.
[b]HP = 1-hexyl-2,5-dimethyl-1H-pyrrole (hexyl pyrrole)
[c]HBP = 1,6-bis(2,5-dimethyl-1H-pyrrol-1-yl)hexane (hexamethylene bispyrrole)
[d]PPTMS = 2,5-dimethyl-1-(3-(trimethoxysilyl)propyl)-1H-pyrrole (pyrrolopropyl trimethoxysilane)

The invention claimed is:

1. An adduct of a compound of formula (I)

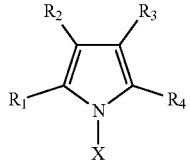
(I)

wherein $R_1$, $R_2$, $R_3$, $R_4$ are independently chosen from: hydrogen, $C_1$-$C_3$ alkyl, $C_2$-$C_{18}$ linear or branched alkenyl, $C_2$-$C_{18}$ linear or branched alkynyl, aryl, $C_1$-$C_{18}$ linear or branched alkyl-aryl, $C_2$-$C_{18}$ linear or branched alkenyl-aryl, $C_2$-$C_{18}$ linear or branched alkynyl-aryl, and heteroaryl; and X is chosen from:

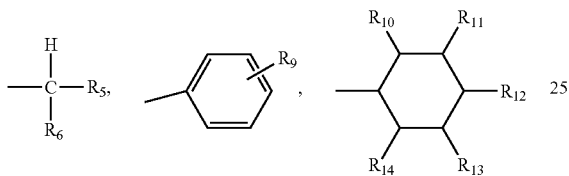

wherein $R_5$ and $R_6$ are independently chosen from: hydrogen, $C_1$-$C_{18}$ alkyl, $C_2$-$C_{18}$ linear or branched alkenyl, $C_2$-$C_{18}$ linear or branched alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, and heteroaryl; or $R_5$ or $R_6$ are each or both

wherein m is 0, 1, or 2 and n is an integer from 1 to 30, wherein if only one of $R_5$ or $R_6$ is

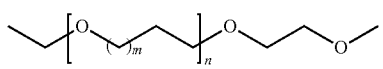

wherein m is 0, 1, or 2 and n is an integer from 1 to 30, then the other is chosen from: hydrogen, $C_1$-$C_{18}$ alkyl, $C_2$-$C_{18}$ linear or branched alkenyl, and $C_2$-$C_{18}$ linear or branched alkynyl; or $R_5$ and/or $R_6$ are:

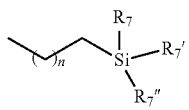

wherein n is 0, 1, 2, or 3 and $R_7$, $R_7'$, $R_7''$ are independently chosen from: $C_1$-$C_4$ alkyl, and oxygen-alkyl $C_1$-$C_4$; or $R_5$ and/or $R_6$ are:

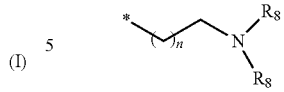

wherein n is 0, 1, 2, or 3 and $R_8$ is $C_1$-$C_4$ alkyl; or $R_5$ and/or $R_6$ are:

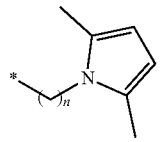

wherein n is an integer from 1 to 10;
$R_9$ is chosen from: hydrogen, alkyl, aryl, benzyl, amine, alkylamine, arylamine, benzylamine, and aminoaryl;
$R_{10}$, $R_{11}$, $R_{12}$, $R_{13}$, and $R_{14}$ are independently chosen from: hydrogen, $C_1$-$C_{18}$ alkyl, $C_2$-$C_{18}$ linear or branched alkenyl, $C_2$-$C_{18}$ linear or branched alkynyl, and 1-(4-aminocyclohexyl)methylene;
and a carbon allotrope containing carbon atoms hybridized $sp^2$ or a derivative thereof, and
wherein the carbon allotrope derivative comprises functional groups chosen from:
oxygenated functional groups;
functional groups containing carbonyls;
functional groups containing nitrogen atoms; and
functional groups containing sulfur atoms.

2. The adduct according to claim 1, wherein $R_1$, $R_2$, $R_3$, and $R_4$ are independently chosen from: H, CH3, CH2CH3, and phenyl.

3. The adduct according to claim 1, wherein the carbon allotrope or the derivative thereof is chosen from: carbon black, fullerene, single-wall or multiwall carbon nanotubes, graphene, and graphite with a number of graphene layers ranging from 2 to 10000.

4. The adduct according to claim 1, wherein the carbon allotrope derivative is graphite oxide.

5. The adduct according to claim 1, wherein the carbon allotrope derivative is graphene oxide.

6. A process for preparing an adduct of a compound of formula (I) according to claim 1, the process comprising:
   i. providing a solution of the compound of formula (I) in a protic or aprotic polar solvent;
   ii. providing a suspension of the carbon allotrope in the protic or aprotic polar solvent used for the preparation of the solution referred to in step i.;
   iii. mixing the solution and the suspension to form a mixture;
   iv. removing the solvent from the mixture; and
   v. providing energy in a form chosen from thermal, mechanical, photon irradiation, and combinations thereof, to the mixture.

7. The process according to claim 6, wherein the energy is thermal and is provided at a temperature ranging from 50 to 180° C. and for a time ranging from 15 to 360 minutes.

8. The process according to claim 6, wherein the energy is mechanical and is provided for a time ranging from 15 to 360 minutes.

9. The process according to claim 6, wherein the energy is photon irradiation and is provided at a wavelength ranging from 200 to 380 nm and for a time ranging from 30 to 180 minutes.

* * * * *